US012135274B2

(12) United States Patent
Dembski

(10) Patent No.: US 12,135,274 B2
(45) Date of Patent: Nov. 5, 2024

(54) OUTLET FITTINGS FOR REDUCING BUBBLES AT THE INTERFACE WITH A FLOW CELL, AND FLOW CYTOMETERS AND METHODS USING THE SAME

(71) Applicant: Becton, Dickinson and Company, Franklin Lakes, NJ (US)

(72) Inventor: Kyle Dembski, Scotts Valley, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/867,394

(22) Filed: Jul. 18, 2022

(65) Prior Publication Data

US 2023/0046207 A1    Feb. 16, 2023

Related U.S. Application Data

(60) Provisional application No. 63/231,403, filed on Aug. 10, 2021.

(51) Int. Cl.
| | |
|---|---|
| *G01N 15/1434* | (2024.01) |
| *G01N 15/10* | (2024.01) |
| *G01N 15/1404* | (2024.01) |
| *G01N 33/487* | (2006.01) |

(52) U.S. Cl.
CPC ..... *G01N 15/1434* (2013.01); *G01N 15/1404* (2013.01); *G01N 33/487* (2013.01); *G01N 2015/1006* (2013.01)

(58) Field of Classification Search
CPC .......... G01N 15/1434; G01N 15/1404; G01N 33/487; G01N 2015/1006
See application file for complete search history.

(56) References Cited

U.S. PATENT DOCUMENTS

| | | | |
|---|---|---|---|
| 6,110,427 A | 8/2000 | Uffenheimer | |
| 8,094,312 B2 | 1/2012 | Ulmer | |
| 10,253,355 B2* | 4/2019 | Richards | C12Q 1/6841 |
| 2004/0062685 A1* | 4/2004 | Norton | G01N 15/1404 436/63 |
| 2015/0260745 A1* | 9/2015 | Chan | G01N 35/1011 73/864.21 |

(Continued)

FOREIGN PATENT DOCUMENTS

EP    1403633 A2 *   3/2004   ............. G01N 15/14

OTHER PUBLICATIONS

The University of Texas (UTHealth), "Safety Guidelines," https://www.uth.edu/imm/service-centers/flow-cytometry/safety-guidelines, Internet Archive Version from Oct. 28, 2020). (Year: 2020).*

*Primary Examiner* — Uzma Alam
*Assistant Examiner* — Chad Andrew Reverman
(74) *Attorney, Agent, or Firm* — Peter W. Schroen; Bret E. Field; BOZICEVIC, FIELD & FRANCIS LLP

(57) ABSTRACT

Outlet fittings are provided. Outlet fittings of interest include an elongate structure and an opening at a proximal end for receiving a flow stream from the distal end of a flow cell. In addition, the outlet fittings described herein are configured to reduce the formation of bubbles at the interface between the outlet fitting and the flow cell. In certain cases, outlet fittings do not include a planar surface in contact with the received flow stream. Flow cytometers and methods employing the subject outlet fittings are also provided.

20 Claims, 10 Drawing Sheets

(56) References Cited

U.S. PATENT DOCUMENTS

| | | | |
|---|---|---|---|
| 2016/0041083 A1* | 2/2016 | Wanders | G01N 33/80 |
| | | | 435/39 |
| 2016/0326489 A1 | 11/2016 | Durack et al. | |
| 2017/0089881 A1* | 3/2017 | Bahl | G01N 29/2418 |
| 2017/0248508 A1* | 8/2017 | Ward | G01N 33/5091 |
| 2018/0156711 A1* | 6/2018 | Vrane | G01N 15/1404 |
| 2019/0040356 A1* | 2/2019 | Durack | G01N 15/1468 |
| 2021/0199543 A1* | 7/2021 | Fedorov | G01N 1/40 |

* cited by examiner

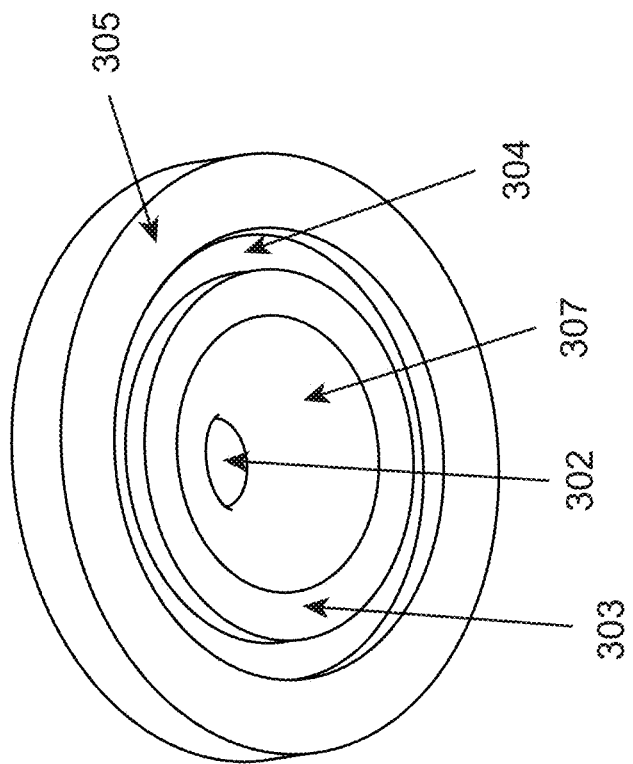
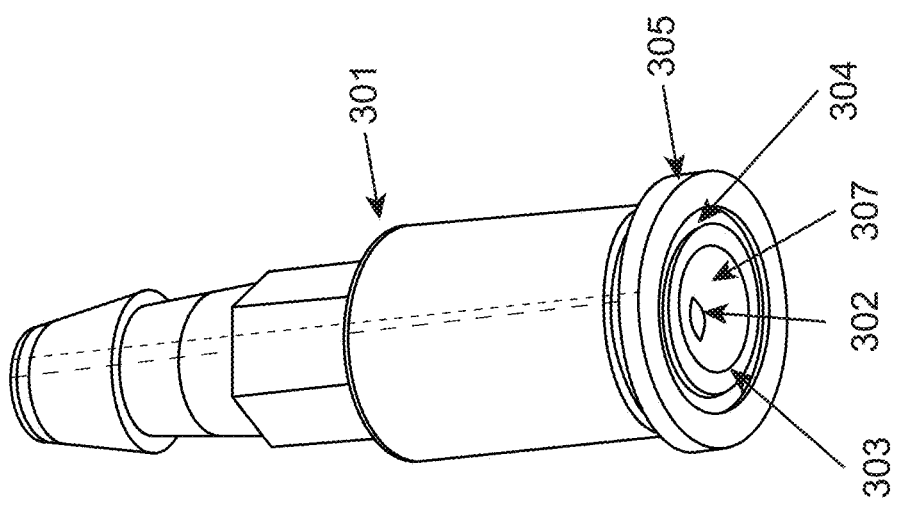
FIG. 3B
FIG. 3A

OUTLET FITTINGS FOR REDUCING BUBBLES AT THE INTERFACE WITH A FLOW CELL, AND FLOW CYTOMETERS AND METHODS USING THE SAME

CROSS-REFERENCE TO RELATED APPLICATION

Pursuant to 35 U.S.C. § 119 (e), this application claims priority to the filing date of U.S. Provisional Patent Application Ser. No. 63/231,403 filed Aug. 10, 2021; the disclosure of which application is incorporated herein by reference in their entirety.

INTRODUCTION

The characterization of analytes in biological fluids has become an important part of biological research, medical diagnoses and assessments of overall health and wellness of a patient. Detecting analytes in biological fluids, such as human blood or blood derived products, can provide results that may play a role in determining a treatment protocol of a patient having a variety of disease conditions.

Particle analysis (e.g., flow cytometry) is a technique used to characterize and often times sort biological material, such as cells of a blood sample or particles of interest in another type of biological or chemical sample. A flow cytometer typically includes a sample reservoir for receiving a fluid sample, such as a blood sample, and a sheath reservoir containing a sheath fluid. The flow cytometer transports the particles (including cells) in the fluid sample as a cell stream to a flow cell, while also directing the sheath fluid to the flow cell. To characterize the components of the flow stream, the flow stream is irradiated with light. Variations in the materials in the flow stream, such as morphologies or the presence of fluorescent labels, may cause variations in the observed light and these variations allow for characterization and separation. To characterize the components in the flow stream, light must impinge on the flow stream and be collected. Light sources in flow cytometers can vary and may include one or more broad spectrum lamps, light emitting diodes as well as single wavelength lasers. The light source is aligned with the flow stream and an optical response from the illuminated particles is collected and quantified.

The parameters measured using a particle analyzer typically include light at the excitation wavelength scattered by the particle in a narrow angle along a mostly forward direction, referred to as forward-scatter (FSC), the excitation light that is scattered by the particle in an orthogonal direction to the excitation laser, referred to as side-scatter (SSC), and the light emitted from fluorescent molecules or fluorescent dye. Different cell types can be identified by their light scatter characteristics and fluorescence emissions resulting from labeling various cell proteins or other constituents with fluorescent dye-labeled antibodies or other fluorescent probes. Forward-scattered light, side-scattered light and fluorescent light is detected by photodetectors that are positioned within the particle analyzer.

In some flow cytometers, a sheath fluid is provided to the flow cell by a pressure driven fluidics system where the sample fluid and sheath fluid are passed through the flow cell under pressure greater than ambient pressure. Changes in the flow rate through the flow cell are achieved by varying the pressure in the sheath fluid reservoir and the ratio of sample fluid to sheath fluid in hydrodynamic flow is determined by the exerted pressure in the sample source and sheath fluid reservoir, as well as by the resistance of the fluidic system supplying the sample and sheath fluid. Flow cytometers can also use a vacuum-driven fluidics system where a vacuum pump draws vacuum downstream from the flow cell and the sample and sheath fluids remain at ambient pressure. To change the rate through the flow cell, vacuum is drawn by the vacuum pump and the ratio of sample fluid to sheath fluid that flows through the flow cell is determined by the ratio of the resistance exerted by the paths of the sample fluid and sheath fluid systems. Fluidic systems providing a hydrodynamically focused flow of particle-containing sample fluid in the center of a particle-free sheath fluid stream often utilize pressurizable tubings, connections and seals that are required to withstand wide ranges of pressure levels, in particular high and low pressures. Aspects of fluid management may be based on the fluid circuit principle, where the pressure drop across a closed fluid pathway is assumed equal to the product of liquid flowrate and fluid resistance.

Some flow cytometers having the above-described fluidics systems include an outlet fitting positioned at the distal end of the flow cell. Such outlet fittings include an opening for receiving fluid from the flow stream following its passage through the flow cell. The received fluid is subsequently transported through the outlet fitting to a waste container. The outlet fitting mates with the flow cell (e.g., with a cuvette in the flow cell) and creates a seal so that the pressure within the fluidics system may be manipulated in order to drive fluid through the flow cell. For example, FIG. 1A depicts a fluidic system 100 having a flow cell 102 and a cuvette 103 positioned therein. In the example of FIG. 1A, fluid is transported in direction d (i.e., in an upwards direction) via a vacuum and contacts outlet fitting 101. As shown in FIG. 1B outlet fitting 101 has an opening 104 for receiving fluid from the flow cell 102. Surrounding opening 104 is a planar surface 105 as well as a gap 106 between the planar surface 105 and a rim portion 107.

SUMMARY

The present inventor has discovered that the use of conventional outlet fittings (e.g., such as those described above and depicted in FIG. 1A-B) involves a series of complications that compromises the quality of data produced by the flow cytometer. In particular, the inventor realized that such outlet fittings are susceptible to trapping air bubbles at the interface between the flow cell and the outlet fitting. Such bubbles may occlude the opening and thereby affect the manner in which pressure is regulated within the fluidics system. For example, trapped air bubbles cause an increase in resistance measured by a pressure transducer (i.e., a device evaluating the pressure differential across the flow cell cuvette). When resistance changes, the pressure differential (i.e., between the sample pressure and sheath fluid pressure) changes. The system reacts to correct the pressure differential such that it returns to its calibrated setting by increasing or decreasing the vacuum pressure. If the system decreases vacuum pressure to correct the differential, the flow rate decreases. The decrease in flow rate is further compounded by the increase in resistance. These impacts to the flow rate are directly related to laser delay. In other words, the intended timing with which the sample particles in the flow stream are irradiated by the laser is offset. In some cases, such laser delay results in only certain portions of a particle being irradiated, thereby reducing the quality of the data collected therefrom. In view of the discovered complications with respect to conventional outlet fittings, the present inventor has realized that improved outlet fittings are desired. Embodiments of the present invention satisfy this desire.

Aspects of the disclosure include outlet fittings having an elongate structure and an opening at a proximal end for receiving a flow stream from the distal end of a flow cell. Outlet fittings of interest are configured to reduce the formation of bubbles at the interface between the outlet fitting and the flow cell, and operably couple to a waste line at a distal end. In embodiments, the outlet fitting does not include a planar surface that is orthogonal to the direction of fluid flow of the received flow stream. For example, in some instances, the outlet fitting includes an annular lip surrounding the opening for establishing a gapless interface between the outlet fitting and the distal end of the flow cell. Embodiments of the annular lip are configured to engage in a face seal with the flow cell, and have a diameter ranging from 1.5 mm to 2.5 mm, such as 1.6 mm to 2 mm. In some cases, the disclosed outlet fitting has a tapered opening either in addition to or instead of the annular lip. Where the outlet fittings include a tapered opening, embodiments of the opening have a taper angle ranging from 1° to 60°, such as 1° to 20°. The opening may have any suitable diameter. Diameters of interest range from 0.5 mm to 2.5 mm, such as 0.5 mm to 0.7 mm. In some cases, the outlet fitting includes an O-ring groove. Outlet fittings may include any convenient material, including, but not limited to, a polymeric material (e.g., polyether ether ketone (PEEK)).

Aspects of the invention additionally include flow cytometers. Flow cytometers of interest include a flow cell having a flow channel for transporting particles in a flow stream therethrough from an inlet at a proximal end to an outlet at a distal end, a light source for irradiating the flow stream at an interrogation point, a detector configured to receive particle-modulated light from the flow stream, and an outlet fitting. As discussed above, the subject outlet fittings have an elongate structure and an opening at a proximal end for receiving the flow stream from the distal end of the flow cell and are configured to reduce the formation of bubbles at the interface between the outlet fitting and the flow cell. In certain cases, flow cytometers include an O-ring that is matched to the size of an O-ring groove in the outlet fitting. Flow cytometers may, in some embodiments, include a waste line operably coupled to the outlet fitting as well as a vacuum source operably coupled to the waste line. In some embodiments, the flow cell includes a cuvette. Aspects of the invention additionally include methods of assembling a flow cytometer having the above components, as well as methods for analyzing a sample in such a flow cytometer.

BRIEF DESCRIPTION OF THE FIGURES

The invention may be best understood from the following detailed description when read in conjunction with the accompanying drawings. Included in the drawings are the following figures:

FIG. 3A-C depict an outlet fitting having a tapered opening according to certain embodiments.

DETAILED DESCRIPTION

Figure 1A:
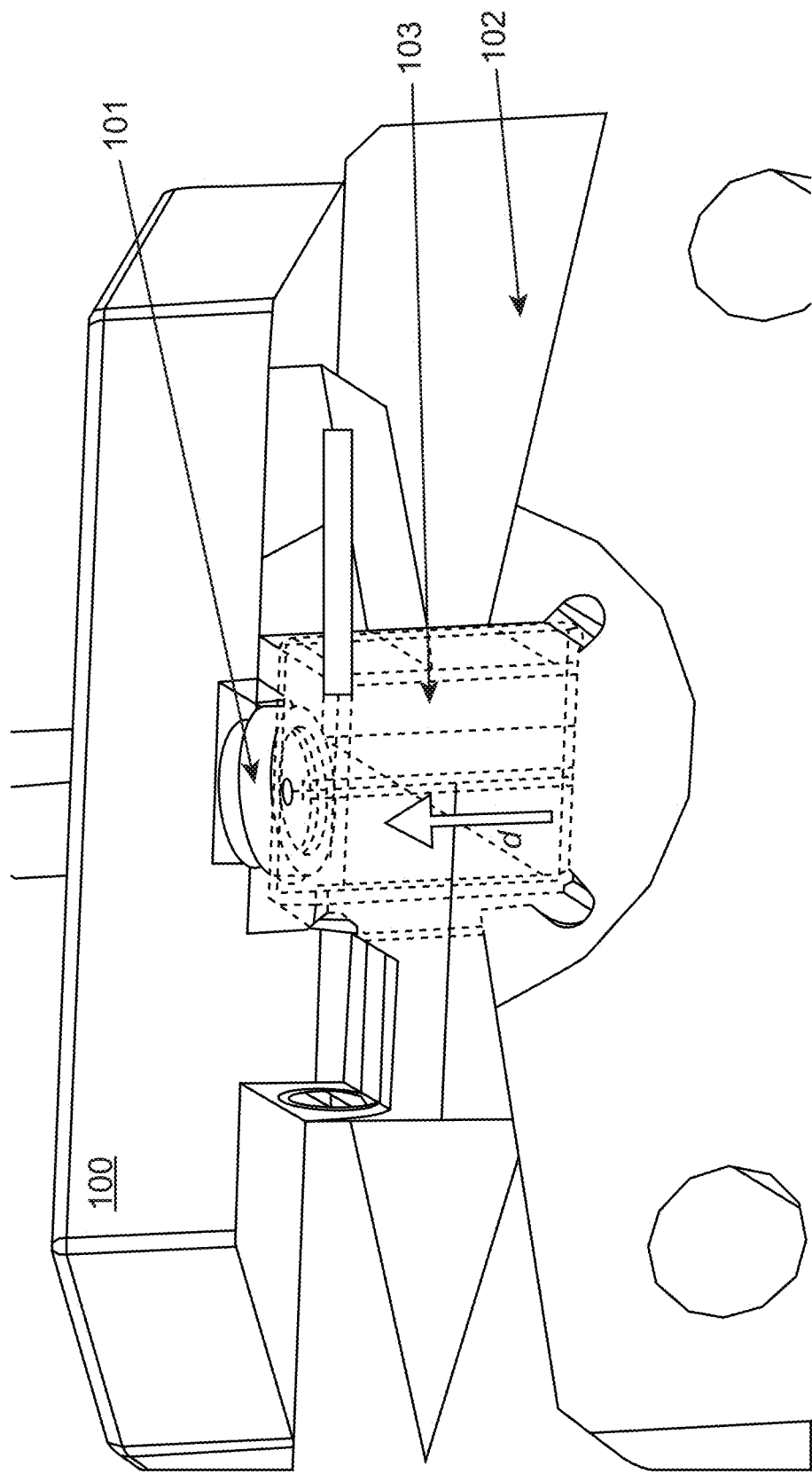
FIG. 1A-B depict a conventional flow cell and outlet fitting.

Outlet fittings are provided. Outlet fittings of interest include an elongate structure and an opening at a proximal end for receiving a flow stream from the distal end of a flow cell. In addition, the outlet fittings described herein are configured to reduce the formation of bubbles at the interface between the outlet fitting and the flow cell. In certain cases, outlet fittings do not include a planar surface that is orthogonal to the direction of fluid flow of the received flow stream. Flow cytometers and methods employing the subject outlet fittings are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the system and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Outlet Fittings

Figure 1B:
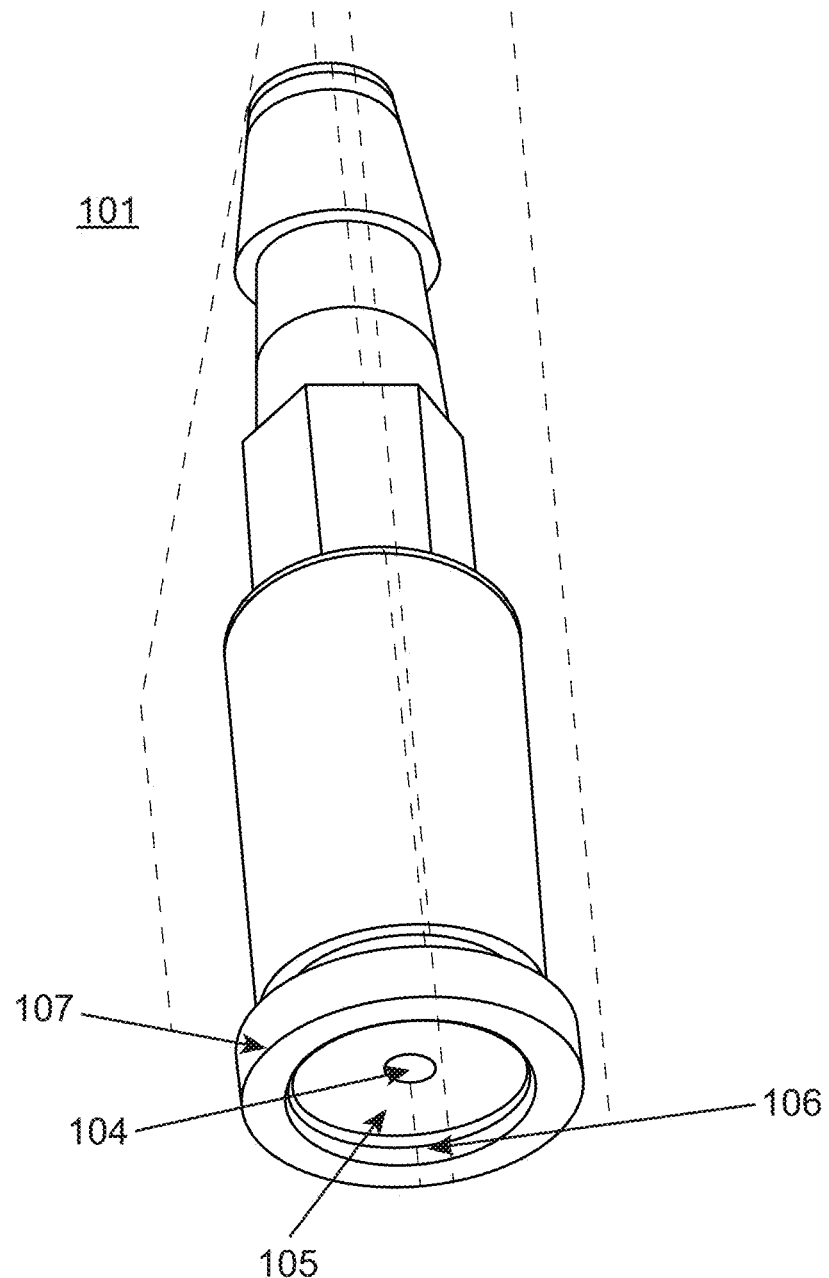

As discussed above, aspects of the invention include outlet fittings for receiving fluid from the distal end of a flow cell. Outlet fittings of interest have an elongate structure and an opening at a proximal end of the elongate structure for receiving a flow stream from the distal end of a flow cell. The outlet fittings described herein are configured to reduce the formation of bubbles at the interface between the outlet fitting and the flow cell (e.g., a cuvette of the flow cell). For example, in some cases, the subject outlet fittings are sufficient to reduce the formation of bubbles by 50% or more, such as 60% or more, such as 70% or more, such as 80% or more, such as 90% or more and including 100%, e.g., as compared to an outlet fitting as shown in FIGS. 1A and 1B. As such, the outlet fittings described herein are sufficient to reduce instances in which fluidic systems decrease flow rate in response to changes in pressure differentials caused by bubbles at the interface between the flow cell and the outlet fitting by 50% or more, such as 60% or more, such as 70% or more, such as 80% or more, such as 90% or more and including 100%, as compared to an outlet fitting as shown in FIGS. 1A and 1B. The outlet fittings of the present disclosure may consequently decrease instances of laser delay.

By "elongate structure" it is meant that the outlet fitting possesses a greater length than width. In other words, the outlet fitting possesses a distinct proximal and distal end. The proximal end is the end at which the outlet fitting receives liquid from the flow stream, while the distal end is the end at which the outlet fitting emits liquid (e.g., so that it may be transported to a waste container). The elongate structure may have any convenient cross-sectional shape, where cross-sectional shapes of interest include, but are not limited to rectilinear cross-sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In embodiments, the elongate structure possesses a substantially circular cross-sectional shape at locations along the length. By "substantially" circular cross-section, it is meant that, in embodiments, one or more locations along the length of the outlet fitting may have a cross-section that slightly deviates from a circular cross-section that characterizes the remainder of the structure. For example, in some versions, the elongate structure has a polygonal (e.g., hexagonal, pentagonal, etc.) cross-section at one or more locations along the length. In certain cases, the width (e.g., cross-sectional diameter) of the elongate structure changes along the length of the outlet fitting. Put another way, in such versions, the elongate structure is not a perfect cylinder and instead possesses some regions having a circular cross-sectional shape with a diameter that is larger than those of other regions. For example, the cross-sectional diameter of the elongate structure may range (e.g., at one or more distinct points along the length of the structure) from 1.5 mm to 3.5 mm, such as 1.7 mm to 3.2 mm, and including 1.8 mm to 3.1 mm. The elongate structure may have any suitable length. For example, in some instances, the length of the elongate structure ranges from 10 mm to 20 mm such as 12 mm to 18 mm and including 14 mm to 16 mm. In certain versions, the elongate structure has a length of 14.7 mm.

Outlet fittings of interest include an opening at the proximal end and a channel running therethrough that connects the opening to the distal end of the elongate structure. In embodiments, the opening is located at the geometric center of the cross-section of the outlet fitting at the proximal end. In such embodiments, the channel connecting the opening to the distal end is similarly located in the geometric center of the elongate structure. The opening may have any convenient cross-sectional shape, where cross-sectional shapes of interest include, but are not limited to rectilinear cross-sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In certain cases, the opening has a circular cross-sectional shape. In additional cases, the channel similarly includes a circular cross-sectional shape. The opening, may have any suitable diameter, such as where the diameter ranges from 0.5 mm to 2.5 mm, such as 0.5 mm to 2 mm, and including 0.5 mm to 0.7 mm. In some cases, the opening has a diameter of 0.61 mm. Similarly, the channel may have any suitable diameter, such as where the diameter ranges from 0.5 mm to 2.5 mm, such as 0.5 mm to 2 mm, and including 0.5 mm to 0.7 mm. In some versions, the channel has a diameter of 0.61 mm. In some cases, the opening and the channel possess a circular cross-sectional shape having the same or similar diameter. In other cases, the opening has a diameter that is different (e.g., larger) than the diameter of the channel. In certain cases, the outlet fitting possesses a raised rim portion at the proximal end. The rim portion may be employed, for example, to generate a seal around the fluidics system such that pressure applied to the system does not escape at the junction between the outlet fitting and the flow cell.

As discussed above, outlet fittings of the present disclosure are configured to reduce the formation of bubbles at the interface between the outlet fitting and the flow cell. To this end, embodiments of the outlet fitting do not include a planar surface that is orthogonal to the direction of fluid flow of the received flow stream. As discussed herein, a "planar surface" refers to a portion at the proximal end of a conventional outlet fitting that is configured to interface with the flow cell and contacts at least a portion of the flow stream (e.g., bubbles present in the flow stream). The planar surface is flat, i.e., exists within a single plane. In other words, while a rim portion (e.g., rim portion 107 shown in FIG. 1B) does not contact the flow stream and is consequently not a constituent of the planar surface, a flat surface circumscribed by the rim portion is considered a planar surface.

For example, in some versions, the outlet fitting includes an annular lip surrounding the opening for establishing a gapless interface between the outlet fitting and the distal end of the flow cell. By "gapless interface" it is meant that there is minimal (including zero) distance that liquid in the flow stream must travel between a plane defined by the rim portion of the outlet fitting and the opening. Put another way, in embodiments, the annular lip extends the location of the opening into the interface between the outlet fitting and the flow cell, i.e., such that the location of the opening is adjacent to the flow cell (e.g., to a cuvette within the flow cell). In some embodiments, the annular lip extends the location of the opening such that the opening and the rim portion exist in approximately the same plane. By "approximately" the same plane, it is meant that the opening extended by the annular lip and the rim portion may exist in planes that differ in location by 50 μm or less, such as 40 μm or less, such as 30 μm or less, such as 20 μm or less, such as 10 μm or less, such as 5 μm or less, such as 3 μm or less, such as 1 μm or less, such as 0.5 μm or less and including where the annular lip and the rim portion exist in the same plane. The annular lip may have any convenient dimensions. As an annulus, the annular lip may be defined in terms of an inner diameter (i.e., measured from the geometric center to the inner edge) and an outer diameter (i.e., measured from the geometric center to the outer edge). Because the annular lip surrounds the opening, the inner diameter of the annular lip possesses the same dimensions as the opening (e.g., such as those presented above). The outer diameter of the annular lip, on the other hand, may range in embodiments from 1 mm to 3 mm, such as 1.5 mm to 2.5 mm, and including 1.6 to 2 mm. In some cases, the outer diameter of the annular lip is 1.8 mm. Because the annular lip constitutes a variation in the topography of the proximal end of the outlet fitting (e.g., circumscribed by the rim portion), an outlet fitting having an annular lip does not possess a planar surface as defined above.

In certain versions, the annular lip is configured to engage in a face seal with the flow cell (e.g., with a cuvette in the flow cell). By "face seal" it is meant that the surface of the annular lip is a sealing surface that is normal to the axis of the flow stream. In embodiments, the annular lip is in contact with a different sealing surface on the flow cell that is similarly normal to the of the flow stream. The face seal prevents the loss of pressure and/or liquid passing therethrough in a radial direction with respect to the interface between the flow cell and the outlet fitting. The annular lip may have a surface of any convenient size, such as where the surface has an area ranging from 2 $mm^2$ to 25 $mm^2$, such as 3 $mm^2$ to 15 $mm^2$, and including 7 $mm^2$ to 11 $mm^2$. In embodiments, the surface of the annular lip has an area of 9 $mm^2$. In some embodiments, such as where the annular lip and the rim portion of the outlet fitting exist on the same plane, both the annular lip and the rim portion form a face seal with respect to the flow cell.

In some cases, the outlet fitting additionally includes a sealing element groove. As discussed herein, a sealing element is a component, such an O-ring, configured to maintain the integrity of the seal between the outlet fitting and the flow cell. In some versions, the sealing element groove includes an O-ring groove, i.e., a groove sized to receive an O-ring. In certain embodiments, the O-ring groove is a circular groove situated between the annular lip and the rim portion.

Figure 2A:
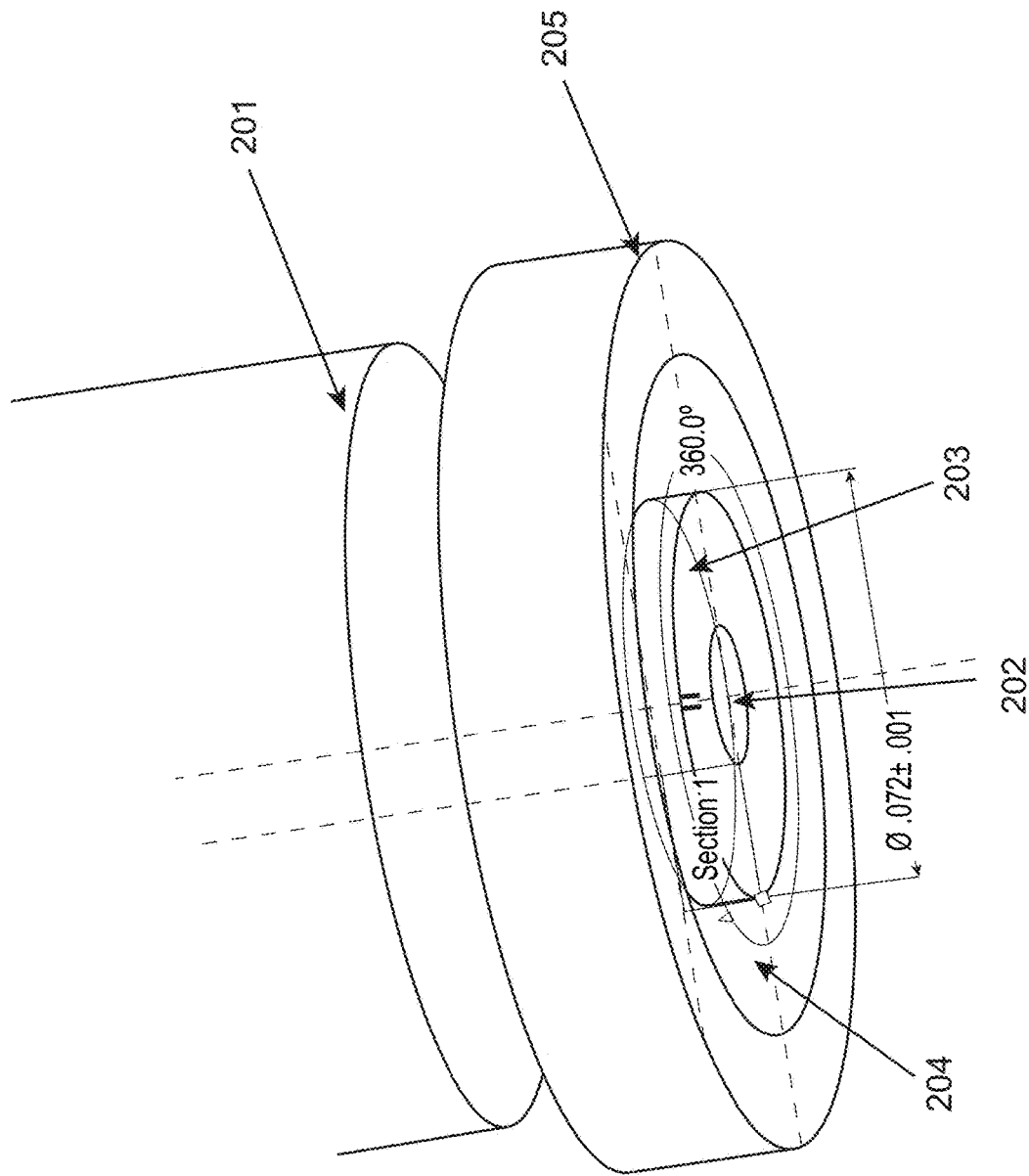
FIG. 2A-B depict an outlet fitting having an annular lip according to certain embodiments.
Figure 2B:
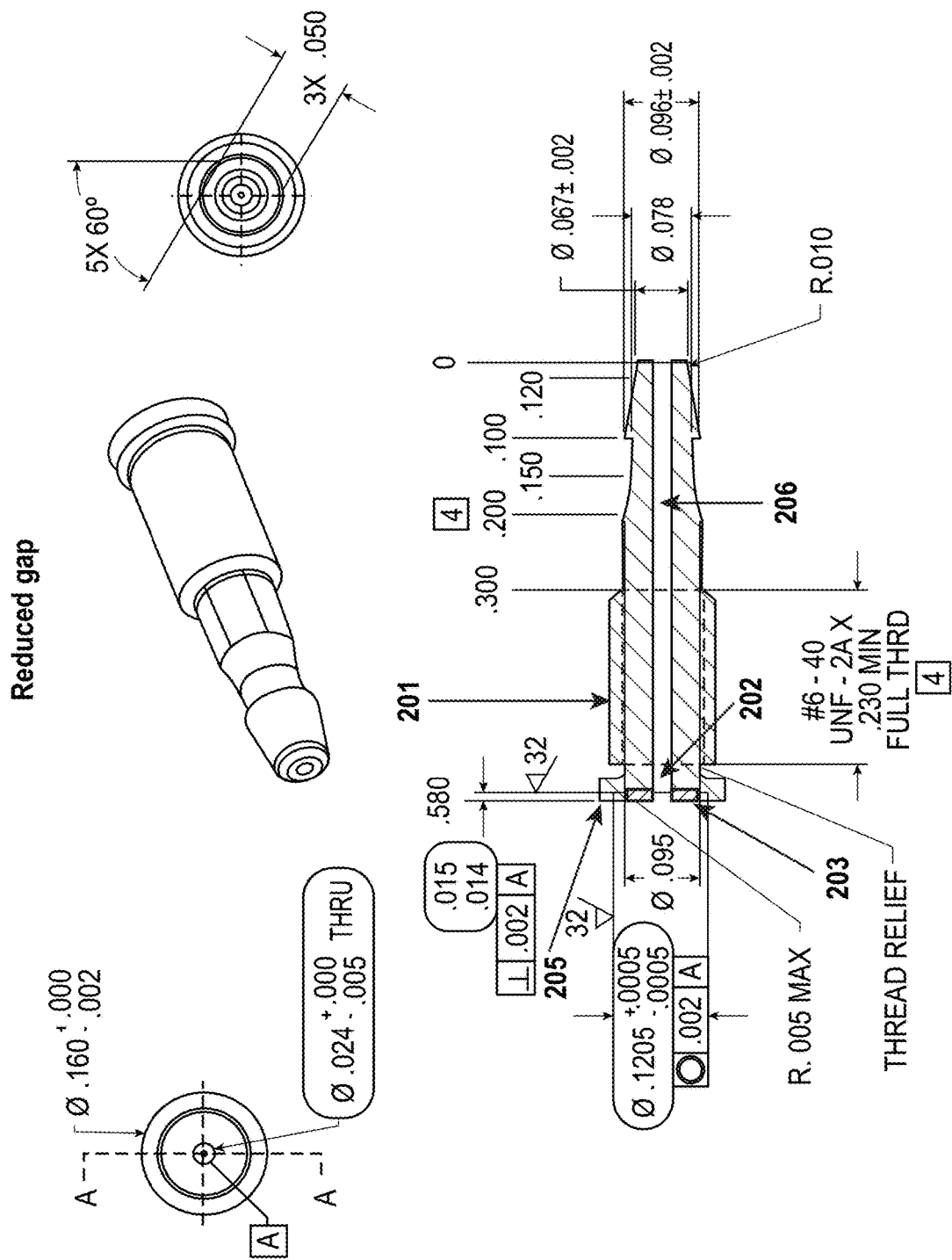

FIG. 2A-B depict an outlet fitting having an annular lip according to certain embodiments of the invention. The proximal end of outlet fitting 201 is depicted in FIG. 2A. Outlet fitting 201 includes opening 202 surrounded by annular lip 203. Opening 202 is extended into the interface between the outlet fitting 201 and the flow cell (not shown) by annular lip 203. Also included is a rim portion 205. In the example of FIG. 2A, rim portion 205 and annular lip 203 exist on the same plane. Between rim portion 205 and annular lip 203 is O-ring groove 204. When outlet fitting 201 is applied to the flow cell in order to create a seal, O-ring groove 204 is configured to receive and O-ring and thereby prevent the escape of pressure and/or fluid in a radial direction. FIG. 2B presents a lengthwise view of the interior of the outlet fitting. In addition to the components described above with respect to FIG. 2A, FIG. 2B depicts channel 206 connecting opening 202 to the distal end.

In some embodiments, the outlet fitting includes a tapered opening. By "tapered opening" it is meant that the opening is wide at the proximal-most end of the outlet fitting and continues to narrow along the length. In certain cases, the opening is frustum-shaped. For example, in some versions, the opening has a frustoconical shape (i.e., having the shape of a frustum of a cone). The opening subsequently terminates at the channel of the outlet fitting, which continues through the outlet fitting to the distal end. The opening may have any convenient taper angle. As discussed herein, a "taper angle" refers to the angle with which the opening narrows. For example, where the opening is frustoconical, the taper angle may be determined by the angle between a generatrix line of the conical frustum and the base of the frustum. Any suitable taper angle may be employed, such as where the taper angle ranges from 1° to 60°, including 1° to 20°. In some cases, the taper angle changes from the proximal-most location of the opening to an interior location of the opening. For example, in certain cases, the taper angle may grow larger from the proximal-most location of the opening to an interior location of the opening. In other cases, the taper angle may grow smaller from the proximal-most location of the opening to an interior location of the opening. Because a tapered opening constitutes a variation in the topography of the proximal end of the outlet fitting (e.g., circumscribed by the rim portion), an outlet fitting having a tapered opening does not possess a planar surface as defined above.

A tapered opening may be employed in the outlet fitting instead of, or in addition to, the annular lip. In some instances, the outlet fitting only includes an annular lip. In other instances, the outlet fitting only includes a tapered opening. In still other instances, the outlet fitting includes both an annular lip and a tapered opening. In some instances where the outlet fitting only includes a tapered opening, the taper angle ranges from 1° to 60°. In some instances where the outlet fitting includes both an annular lip and a tapered opening, the taper angle ranges from 1° to 20°.

Figure 3C:
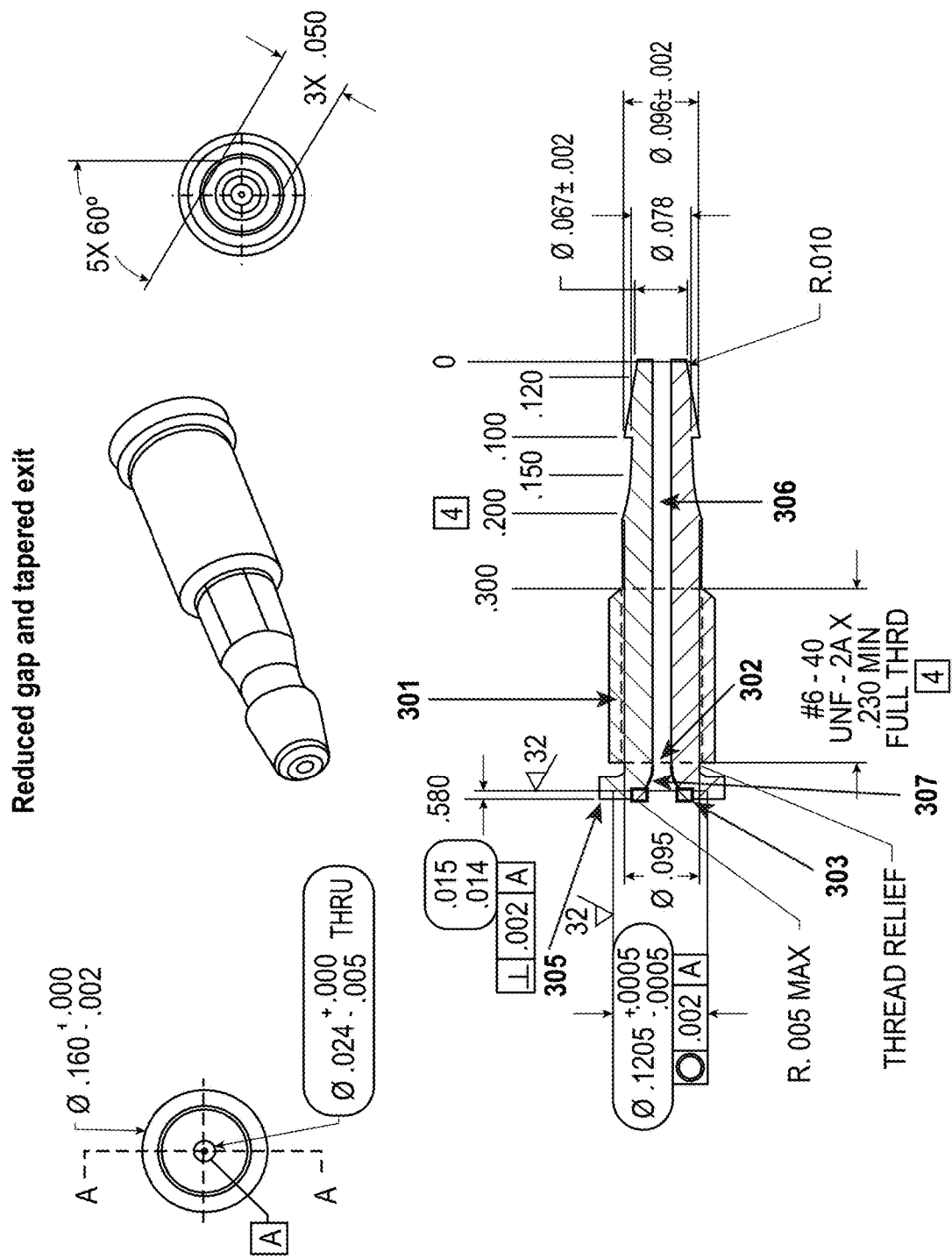

FIG. 3A-C depict an outlet fitting having a tapered opening according to certain embodiments of the invention. As shown in FIG. 3A, the proximal end of outlet fitting 301 includes opening 302 having tapered wall 307. Opening 302 has a frustoconical shape and is surrounded by annular lip 303. Also included is rim portion 305 as well as O-ring groove 304 situated between rim portion 305 and annular lip 303. FIG. 3B presents an enlarged view of the proximal end of outlet fitting 301 depicted in FIG. 3A. presents a lengthwise view of the interior of the outlet fitting. In addition to the components described above with respect to FIG. 3A-B, FIG. 3C depicts channel 306 connecting opening 302 to the distal end.

In certain cases, the outlet fitting is configured to have a waste line attached thereto. As discussed herein, a "waste line" is a fluidic line (e.g., conduit) through which liquid received by the outlet fitting from the flow stream is directed to a suitable disposal location (e.g., a waste container). As such, in embodiments, the outlet fitting includes a connector at the distal end for providing a connection with the waste line. The connector may be any suitable fitting or connector including, e.g., a quick disconnect connector, threaded connector, luer connector, multiport connector, tri clamp fittings, and puncture and seal sterile fittings. Suitable quick disconnect connectors include, but are not limited to, snap-type (ball-latching) connectors, bayonet connectors, threaded connectors, non-latching connectors, single-shutoff connectors, double-shutoff connectors, non-shutoff connectors, dry break connectors, roller lock connectors, pin lock connectors, ring lock connectors, and cam lock connectors.

The subject outlet fittings may be comprised of any convenient material. In certain instances, outlet fittings include one or more polymeric materials. For example, in some embodiments, outlet fittings include one or more rigid plastic materials such as, for example, polycarbonates, polyvinyl chloride (PVC), polyurethanes, polyethers, polyamides, polyimides, among other polymeric plastic materials. Examples of polymeric materials include acrylonitrile butadiene styrene (ABS), polylactic acid (PLA), acrylic styrene acrylonitrile (ASA), polyethylene terephthalate (PET), glycol-modified polyethylene terephthalate (PETG), polyaryletherketones (PAEK), polyetherimides (PEI), poly-polycarbonate (PC), polypropylene, (PP), aliphatic polyamides (PPA), polyoxymethylene (POM), polymethyl methacrylate (PMMA), polybutylene terephthalate (PBT), polyphenylsulfone (PPSU), polyether ether ketone (PEEK), and nylon as well as composites and hybrids thereof. In certain cases, the outlet fitting is composed of PEEK. In some embodiments, the outlet fitting includes a glass-filled polymer (i.e. having glass fibers in a matrix of polymeric material). In such embodiments, any suitable polymer (e.g., such as those described above) may be combined with glass fibers to generate a glass filled polymer.

Figure 4:
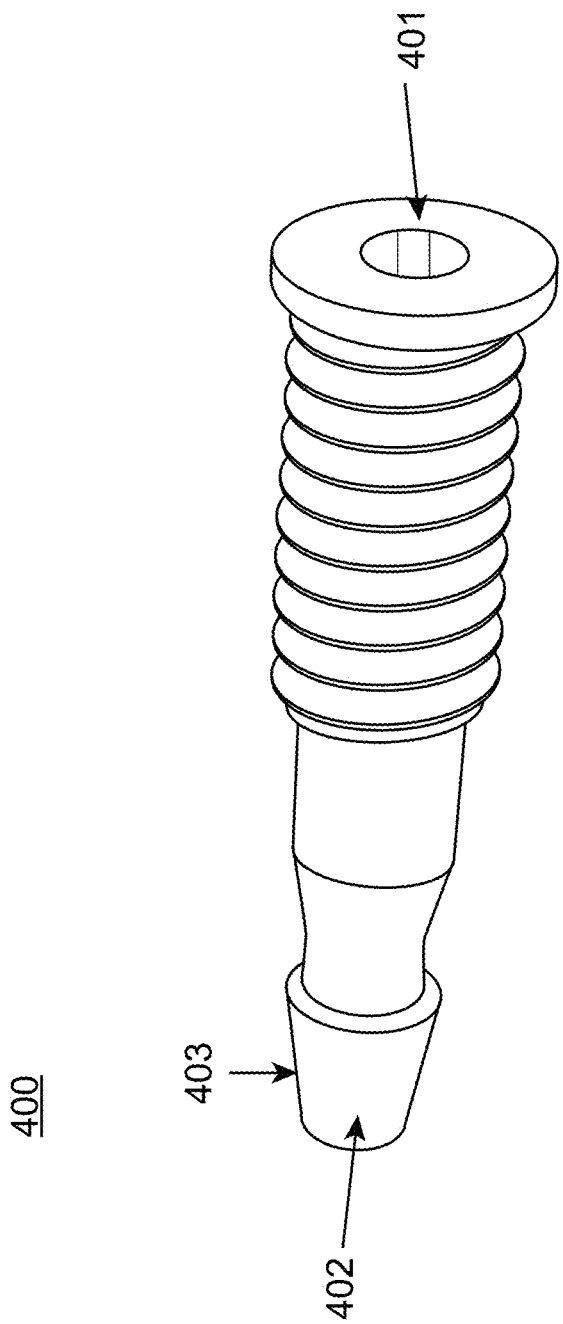
FIG. 4 depicts an outlet fitting according to certain embodiments.

FIG. 4 depicts an outlet fitting according to embodiments of the invention. In the example of FIG. 4, outlet fitting 400 is machined out of polyether ether ketone (PEEK) and possesses proximal end 401 and distal end 402. Distal end 402 includes a connector 403 for connecting the outlet fitting 400 to a waste line (not shown).

Flow Cytometers

Aspects of the invention additionally include flow cytometers. Flow cytometers of interest include a flow cell having a flow channel for transporting particles in a flow stream therethrough from an inlet at a proximal end to an outlet at a distal end, a light source for irradiating the flow stream at an interrogation point, a detector for receiving particle-modulated light from the flow stream, and an outlet fitting. As discussed above, outlet fittings of interest include an elongate structure and an opening at a proximal end for receiving the flow stream from the distal end of the flow cell. Outlet fittings described herein are additionally configured to reduce the formation of bubbles at the interface between the outlet fitting and the flow cell, and operably couple to a waste line at a distal end. In certain cases, the disclosed outlet fittings do not include a planar surface in contact with the received flow stream. For example, in some instances, the outlet fitting includes an annular lip surrounding the opening for establishing a gapless interface between the outlet fitting and the distal end of the flow cell. In additional cases, the opening is tapered.

In some embodiments, the outlet fittings discussed herein have a waste line attached thereto via a connector (e.g., such as those discussed above). The waste line may have any suitable configuration; for example, the waste line may be a tubular fluidic line. In some cases, the fluidic line is a rigid fluidic line. In certain embodiments, the waste line is a pliant, i.e., flexible, fluidic line. The waste line may be made of any suitable material, where such materials include, but are not limited to, a rigid plastic, polymeric or thermoplastic material. For example, suitable plastics may include polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. The waste line may have any convenient length. In some cases, the length of the waste line ranges from 5 cm to 50 cm, such as, e.g., from 5 cm to 40 cm, from 5 cm to 30 cm, from 5 cm to 20 cm, or from 5 cm to 10 cm. The waste line may have any convenient diameter. In some cases, the inner diameter of the waste line ranges from 1 mm to 20 mm such as, e.g., from 1 mm to 15 mm, from 1 mm to 10 mm, from 1 mm to 5 mm, or from 1 mm to 2 mm. In some instances, the waste line coupling the outlet fitting to the waste container includes a resistor. The resistor may provide a known fluid resistance. Suitable resistors include, but are not limited to, a section of tubing with known length and internal diameter, an orifice, etc.

In some embodiments, the flow cytometer includes a waste fluid container. The waste container may be any suitable reservoir or container (e.g., having rigid or flexible walls) for storing waste fluids. In some instances, the distal end of the outlet fitting is fluidically coupled to the waste fluid container. The waste line (e.g., a tube or conduit) may fluidically couple the distal end of the outlet fitting to the waste container. Waste fluid may be flowed out of the outlet fitting and into the waste fluid container, e.g., for storage. In some instances, the waste fluid container is detachable from a waste line that couples it to the outlet fitting such that, e.g., the waste fluid container may be emptied and cleaned. The waste fluid container may be configured to, e.g., have a suitable volume to, contain and store all system fluids. The waste fluid container may have a volume ranging from 1 L to 100 L; for example, the volume of the container may range from 1 L to 90 L, from 1 L to 80 L, from 1 L to 70 L, from 1 L to 60 L, from 1 L to 50 L, from 1 L to 40 L, from 1 L to 30 L, from 1 L to 20 L, or from 1 L to 10 L.

Where desired, flow cytometers may include a fluid movement device configured to convey, e.g., mechanically convey, fluid from the flow stream through the outlet fitting and to the waste fluid container. In some instances, the combined waste fluid is managed by a fluid movement device, e.g., a pump. In some instances, the fluid movement device is a vacuum source that draws the waste fluid from the outlet fitting to the waste fluid container. In some instances, the pump includes a positive displacement vacuum pump. In some instances, the positive displacement vacuum pump includes a pump selected from a diaphragm pump, gear pump and a peristaltic pump. In some instances, the positive displacement vacuum pump is a diaphragm pump.

As discussed herein, the "flow cell" is described in its conventional sense to refer to a component containing a flow channel having a liquid flow stream for transporting particles in a sheath fluid. In embodiments, the subject flow cell includes a cuvette. Cuvettes of interest include containers having a passage running therethrough. The flow stream may include a liquid sample injected from a sample tube. Flow cells of interest include a light-accessible flow channel. In some instances, the flow cell includes transparent material (e.g., quartz) that permits the passage of light therethrough. Any convenient flow cell which propagates a fluidic sample to a sample interrogation region may be employed as the flow cell described herein, where in some embodiments, the flow cell includes is a cylindrical flow cell, a frustoconical flow cell or a flow cell that includes a proximal cylindrical portion defining a longitudinal axis and a distal frustoconical portion which terminates in a flat surface having the orifice that is transverse to the longitudinal axis.

In certain embodiments, the flow cytometer includes a sample fluid source. The sample fluid source may be any suitable reservoir or container (e.g., having rigid or flexible walls) for holding a sample fluid. The sample fluid container may have a volume ranging from 1 mL to 100 mL; for example, the volume of the container may range from 1 mL to 90 mL, from 1 mL to 80 mL, from 1 mL to 70 mL, from 1 mL to 60 mL, from 1 mL to 50 mL, from 1 mL to 40 mL, from 1 mL to 30 mL, from 1 mL to 20 mL, or from 1 mL to 10 mL.

In some embodiments, the flow cytometer includes a sheath fluid source. The sheath fluid source many be any suitable reservoir or container (e.g., having rigid or flexible walls) for holding sheath fluid. In certain embodiments, the sheath fluid source is fluidically coupled to the input of the flow cell. The sheath fluid container may have a volume ranging from 1 L to 100 L; for example, the volume of the container may range from 1 L to 90 L, from 1 L to 80 L, from 1 L to 70 L, from 1 L to 60 L, from 1 L to 50 L, from 1 L to 40 L, from 1 L to 30 L, from 1 L to 20 L, or from 1 L to 10 L.

In some embodiments, the flow cell includes a sample injection port configured to provide a sample from the sample fluid source to the flow cell. The sample injection port may be an orifice positioned in a wall of the inner chamber or may be a conduit positioned at the proximal end of the inner chamber. Where the sample injection port is an orifice positioned in a wall of the inner chamber, the sample injection port orifice may be any suitable shape where cross-sectional shapes of interest include, but are not limited to rectilinear cross-sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion. In certain embodiments, the sample injection port has a circular orifice. The size of the sample injection port orifice may vary depending on shape, in certain instances, having an opening ranging from 0.1 mm to 5.0 mm, such as 0.2 to 3.0 mm, such as 0.5 mm to 2.5 mm, such as from 0.75 mm to 2.25 mm, such as from 1 mm to 2 mm and including from 1.25 mm to 1.75 mm, for example 1.5 mm.

In certain instances, the sample injection port is a conduit positioned at a proximal end of the flow cell inner chamber. For example, the sample injection port may be a conduit positioned to have the orifice of the sample injection port in line with the flow cell orifice. Where the sample injection port is a conduit positioned in line with the flow cell orifice, the cross-sectional shape of the sample injection tube may be any suitable shape where cross-sectional shapes of interest include, but are not limited to: rectilinear cross-sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. The orifice of the conduit may vary depending on shape, in certain instances, having an opening ranging from 0.1 mm to 5.0 mm, e.g., 0.2 to 3.0 mm, e.g., 0.5 mm to 2.5 mm, such as from 0.75 mm to 2.25 mm, such as from 1 mm to 2 mm and including from 1.25 mm to 1.75 mm, for example 1.5 mm. The shape of the tip of the sample injection port may be the same or different from the cross-sectional shape of the sample injection tube. For example, the orifice of the sample injection port may include a beveled tip having a bevel angle ranging from 1 degree to 10 degrees, such as from 2 degrees to 9 degrees, such as from 3 degrees to 8 degrees, such as from 4 degrees to 7 degrees and including a bevel angle of 5 degrees.

In some embodiments, the flow cell also includes a sheath fluid injection port configured to provide a sheath fluid from the sheath fluid source to the flow cell. In embodiments, the sheath fluid injection system is configured to provide a flow of sheath fluid to the flow cell inner chamber, for example in conjunction with the sample to produce a laminated flow stream of sheath fluid surrounding the sample flow stream. Depending on the desired characteristics of the flow stream, the rate of sheath fluid conveyed to the flow cell chamber by the may be 25 µL/sec to 2500 µL/sec, such as 50 µL/sec to 1000 µL/sec, and including 75 µL/sec or more to 750 µL/sec.

In some embodiments, the sheath fluid injection port is an orifice positioned in a wall of the inner chamber. The sheath fluid injection port orifice may be any suitable shape where cross-sectional shapes of interest include, but are not limited to rectilinear cross-sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. The size of the sample injection port orifice may vary depending on shape, in certain instances, having an opening ranging from 0.1 mm to 5.0 mm, e.g., 0.2 to 3.0 mm, e.g., 0.5 mm to 2.5 mm, such as from 0.75 mm to 2.25 mm, such as from 1 mm to 2 mm and including from 1.25 mm to 1.75 mm, for example 1.5 mm.

In some embodiments, systems further include a pump in fluid communication with the flow cell to propagate the flow stream through the flow cell. Any convenient fluid pump protocol may be employed to control the flow of the flow stream through the flow cell. In certain instances, systems include a peristaltic pump, such as a peristaltic pump having a pulse damper. The pump in the subject systems is configured to convey fluid through the flow cell at a rate suitable for multi-photon counting of light from the sample in the flow stream. For example, the system may include a pump that is configured to flow sample through the flow cell at a rate that ranges from 1 nL/min to 500 nL/min, such as from 1 nL/min to 250 nL/min, such as from 1 nL/min to 100 nL/min, such as from 2 nL/min to 90 nL/min, such as from 3 nL/min to 80 nL/min, such as from 4 nL/min to 70 nL/min, such as from 5 nL/min to 60 nL/min and including from 10 nL/min to 50 nL/min. In certain embodiments, the flow rate of the flow stream is from 5 nL/min to 6 nL/min.

As discussed above, the flow stream is configured for irradiation with light from a light source at an interrogation point. The flow stream for which the flow channel is configured may include a liquid sample injected from a sample tube. In certain embodiments, the flow stream may include a narrow, rapidly flowing stream of liquid that is arranged such that linearly segregated particles transported therein are separated from each other in a single-file manner. The "interrogation point" discussed herein refers to a region within the flow cell in which the particle is irradiated by light from the light source, e.g., for analysis. The size of the interrogation point may vary as desired. For example, where 0 μm represents the axis of light emitted by the light source, the interrogation point may range from −100 μm to 100 μm, such as −50 μm to 50 μm, such as −25 μm to 40 μm, and including −15 μm to 30 μm.

After particles are irradiated in the flow cell, particle-modulated light may be observed. By "particle-modulated light" it is meant light that is received from the particles in the flow stream following the irradiation of the particles with light from the light source. In some cases, the particle-modulated light is side-scattered light. As discussed herein, side-scattered light refers to light refracted and reflected from the surfaces and internal structures of the particle. In additional embodiments, the particle-modulated light includes forward-scattered light (i.e., light that travels through or around the particle in mostly a forward direction). In still other cases, the particle-modulated light includes fluorescent light (i.e., light emitted from a fluorochrome following irradiation with excitation wavelength light). In embodiments, particle-modulated light includes a combination of side-scatted light, forward-scattered light and fluorescent light.

As discussed above, aspects of the invention also include a light source configured to irradiate particles passing through the flow cell at an interrogation point. Any convenient light source may be employed as the light source described herein. In some embodiments, the light source is a laser. In embodiments, the laser may be any convenient laser, such as a continuous wave laser. For example, the laser may be a diode laser, such as an ultraviolet diode laser, a visible diode laser and a near-infrared diode laser. In other embodiments, the laser may be a helium-neon (HeNe) laser. In some instances, the laser is a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In other instances, the subject flow cytometers include a dye laser, such as a stilbene, coumarin or rhodamine laser. In yet other instances, lasers of interest include a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, the subject flow cytometers include a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof.

Laser light sources according to certain embodiments may also include one or more optical adjustment components. In certain embodiments, the optical adjustment component is located between the light source and the flow cell, and may include any device that is capable of changing the spatial width of irradiation or some other characteristic of irradiation from the light source, such as for example, irradiation direction, wavelength, beam width, beam intensity and focal spot. Optical adjustment protocols may include any convenient device which adjusts one or more characteristics of the light source, including but not limited to lenses, mirrors, filters, fiber optics, wavelength separators, pinholes, slits, collimating protocols and combinations thereof. In certain embodiments, flow cytometers of interest include one or more focusing lenses. The focusing lens, in one example, may be a de-magnifying lens. In still other embodiments, flow cytometers of interest include fiber optics.

Where the optical adjustment component is configured to move, the optical adjustment component may be configured to be moved continuously or in discrete intervals, such as for example in 0.01 μm or greater increments, such as 0.05 μm or greater, such as 0.1 μm or greater, such as 0.5 μm or greater such as 1 μm or greater, such as 10 μm or greater, such as 100 μm or greater, such as 500 μm or greater, such as 1 mm or greater, such as 5 mm or greater, such as 10 mm or greater and including 25 mm or greater increments.

Any displacement protocol may be employed to move the optical adjustment component structures, such as coupled to a moveable support stage or directly with a motor actuated translation stage, leadscrew translation assembly, geared translation device, such as those employing a stepper motor, servo motor, brushless electric motor, brushed DC motor, micro-step drive motor, high resolution stepper motor, among other types of motors.

The light source may be positioned any suitable distance from the flow cell, such as where the light source and the flow cell are separated by 0.005 mm or more, such as 0.01 mm or more, such as 0.05 mm or more, such as 0.1 mm or more, such as 0.5 mm or more, such as 1 mm or more, such as 5 mm or more, such as 10 mm or more, such as 25 mm or more and including at a distance of 100 mm or more. In addition, the light source may be positioned at any suitable angle relative to the flow cell, such as at an angle ranging from 10 degrees to 90 degrees, such as from 15 degrees to 85 degrees, such as from 20 degrees to 80 degrees, such as from 25 degrees to 75 degrees and including from 30 degrees to 60 degrees, for example at a 90 degree angle.

In some embodiments, light sources of interest include a plurality of lasers configured to provide laser light for discrete irradiation of the flow stream, such as 2 lasers or more, such as 3 lasers or more, such as 4 lasers or more, such as 5 lasers or more, such as 10 lasers or more, and including 15 lasers or more configured to provide laser light for discrete irradiation of the flow stream. Depending on the desired wavelengths of light for irradiating the flow stream, each laser may have a specific wavelength that varies from 200 nm to 1500 nm, such as from 250 nm to 1250 nm, such as from 300 nm to 1000 nm, such as from 350 nm to 900 nm and including from 400 nm to 800 nm. In certain embodiments, lasers of interest may include one or more of a 405 nm laser, a 488 nm laser, a 561 nm laser and a 635 nm laser.

As discussed above, particle analyzers of interest may further include one or more particle-modulated light detectors for detecting particle-modulated light intensity data. In some embodiments, the particle-modulated light detector(s) include one or more forward-scattered light detectors configured to detect forward-scattered light. For example, the subject particle analyzers may include 1 forward-scattered light detector or multiple forward-scattered light detectors, such as 2 or more, such as 3 or more, such as 4 or more, and including 5 or more. In certain embodiments, particle analyzers include 1 forward-scattered light detector. In other embodiments, particle analyzers include 2 forward-scattered light detectors.

Any convenient detector for detecting collected light may be used in the forward-scattered light detector described herein. Detectors of interest may include, but are not limited to, optical sensors or detectors, such as active-pixel sensors (APSs), avalanche photodiodes, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes (PMTs), phototransistors, quantum dot photoconductors or photodiodes and combinations thereof, among other detectors. In certain embodiments, the collected light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, the detector is a photomultiplier tube, such as a photomultiplier tube having an active detecting surface area of each region that ranges from 0.01 $cm^2$ to 10 $cm^2$, such as from 0.05 $cm^2$ to 9 $cm^2$, such as from 0.1 $cm^2$ to 8 $cm^2$, such as from 0.5 $cm^2$ to 7 $cm^2$ and including from 1 $cm^2$ to 5 $cm^2$.

In embodiments, the forward-scattered light detector is configured to measure light continuously or in discrete intervals. In some instances, detectors of interest are configured to take measurements of the collected light continuously. In other instances, detectors of interest are configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

In additional embodiments, the one or more particle-modulated light detector(s) may include one or more side-scattered light detectors for detecting side-scatter wavelengths of light (i.e., light refracted and reflected from the surfaces and internal structures of the particle). In some embodiments, particle analyzers include a single side-scattered light detector. In other embodiments, particle analyzers include multiple side-scattered light detectors, such as 2 or more, such as 3 or more, such as 4 or more, and including 5 or more.

Any convenient detector for detecting collected light may be used in the side-scattered light detector described herein. Detectors of interest may include, but are not limited to, optical sensors or detectors, such as active-pixel sensors (APSs), avalanche photodiodes, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes (PMTs), phototransistors, quantum dot photoconductors or photodiodes and combinations thereof, among other detectors. In certain embodiments, the collected light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, the detector is a photomultiplier tube, such as a photomultiplier tube having an active detecting surface area of each region that ranges from 0.01 $cm^2$ to 10 $cm^2$, such as from 0.05 $cm^2$ to 9 $cm^2$, such as from 0.1 $cm^2$ to 8 $cm^2$, such as from 0.5 $cm^2$ to 7 $cm^2$ and including from 1 $cm^2$ to 5 $cm^2$.

In embodiments, the subject particle analyzers also include a fluorescent light detector configured to detect one or more fluorescent wavelengths of light. In other embodiments, particle analyzers include multiple fluorescent light detectors such as 2 or more, such as 3 or more, such as 4 or more, 5 or more, 10 or more, 15 or more, and including 20 or more.

Any convenient detector for detecting collected light may be used in the fluorescent light detector described herein. Detectors of interest may include, but are not limited to, optical sensors or detectors, such as active-pixel sensors (APSs), avalanche photodiodes, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes (PMTs), phototransistors, quantum dot photoconductors or photodiodes and combinations thereof, among other detectors. In certain embodiments, the collected light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, the detector is a photomultiplier tube, such as a photomultiplier tube having an active detecting surface area of each region that ranges from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

Where the subject particle analyzers include multiple fluorescent light detectors, each fluorescent light detector may be the same, or the collection of fluorescent light detectors may be a combination of different types of detectors. For example, where the subject particle analyzers include two fluorescent light detectors, in some embodiments the first fluorescent light detector is a CCD-type device and the second fluorescent light detector (or imaging sensor) is a CMOS-type device. In other embodiments, both the first and second fluorescent light detectors are CCD-type devices. In yet other embodiments, both the first and second fluorescent light detectors are CMOS-type devices. In still other embodiments, the first fluorescent light detector is a CCD-type device and the second fluorescent light detector is a photomultiplier tube (PMT). In still other embodiments, the first fluorescent light detector is a CMOS-type device and the second fluorescent light detector is a photomultiplier tube. In yet other embodiments, both the first and second fluorescent light detectors are photomultiplier tubes.

In embodiments of the present disclosure, fluorescent light detectors of interest are configured to measure collected light at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths. In some embodiments, 2 or more detectors in the particle analyzers as described herein are configured to measure the same or overlapping wavelengths of collected light.

In some embodiments, fluorescent light detectors of interest are configured to measure collected light over a range of wavelengths (e.g., 200 nm-1000 nm). In certain embodiments, detectors of interest are configured to collect spectra of light over a range of wavelengths. For example, particle analyzers may include one or more detectors configured to collect spectra of light over one or more of the wavelength ranges of 200 nm-1000 nm. In yet other embodiments, detectors of interest are configured to measure light emitted by a sample in the flow stream at one or more specific wavelengths. For example, particle analyzers may include one or more detectors configured to measure light at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, one or more detectors may be configured to be paired with specific fluorophores, such as those used with the sample in a fluorescence assay.

In some embodiments, particle analyzers include one or more wavelength separators positioned between the flow cell and the particle-modulated light detector(s). The term "wavelength separator" is used herein in its conventional sense to refer to an optical component that is configured to separate light collected from the sample into predetermined spectral ranges. In some embodiments, particle analyzers include a single wavelength separator. In other embodiments, particle analyzers include a plurality of wavelength separators, such as 2 or more wavelength separators, such as 3 or more, such as 4 or more, such as 5 or more, such as 6 or more, such as 7 or more, such as 8 or more, such as 9 or more, such as 10 or more, such as 15 or more, such as 25 or more, such as 50 or more, such as 75 or more and including 100 or more wavelength separators. In some embodiments, the wavelength separator is configured to separate light collected from the sample into predetermined spectral ranges by passing light having a predetermined spectral range and reflecting one or more remaining spectral ranges of light. In other embodiments, the wavelength separator is configured to separate light collected from the sample into predetermined spectral ranges by passing light having a predetermined spectral range and absorbing one or more remaining spectral ranges of light. In yet other embodiments, the wavelength separator is configured to spatially diffract light collected from the sample into predetermined spectral ranges. Each wavelength separator may be any convenient light separation protocol, such as one or more dichroic mirrors, bandpass filters, diffraction gratings, beam splitters or prisms. In some embodiments, the wavelength separator is a prism. In other embodiments, the wavelength separator is a diffraction grating. In certain embodiments, wavelength separators in the subject light detection systems are dichroic mirrors.

Suitable flow cytometry systems may include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem*. Jan;49 (pt 1):17-28; Linden, et. al., *Semin Throm Hemost*. 2004 October; 30(5):502-11; Alison, et al. *J Pathol*, 2010 December; 222(4):335-344; and Herbig, et al. (2007) *Crit Rev Ther Drug Carrier Syst*. 24(3):203-255; the disclosures of which are incorporated herein by reference. In certain instances, flow cytometry systems of interest include BD Biosciences FACSCanto™ flow cytometer, BD Biosciences FACSCanto™ II flow cytometer, BD Accuri™ flow cytometer, BD Accuri™ C6 Plus flow cytometer, BD Biosciences FACSCelesta™ flow cytometer, BD Biosciences FACSLyric™ flow cytometer, BD Biosciences FACSVerse™ flow cytometer, BD Biosciences FACSymphony™ flow cytometer, BD Biosciences LSRFortessa™ flow cytometer, BD Biosciences LSR-Fortessa™ X-20 flow cytometer, BD Biosciences FACSPresto™ flow cytometer, BD Biosciences FACSVia™ flow cytometer and BD Biosciences FACSCalibur™ cell sorter, a BD Biosciences FACSCount™ cell sorter, BD Biosciences FACSLyric™ cell sorter, BD Biosciences Via™ cell sorter, BD Biosciences Influx™ cell sorter, BD Biosciences Jazz™ cell sorter, BD Biosciences Aria™ cell sorter, BD Biosciences FACSAria™ II cell sorter, BD Biosciences FACSAria™ III cell sorter, BD Biosciences FACSAria™ Fusion cell sorter and BD Biosciences FACSMelody™ cell sorter, BD Biosciences FACSymphony™ S6 cell sorter or the like.

In some embodiments, the subject systems are flow cytometric systems, such those described in U.S. Pat. Nos. 10,663,476; 10,620,111; 10,613,017; 10,605,713; 10,585,031; 10,578,542; 10,578,469; 10,481,074; 10,302,545; 10,145,793; 10,113,967; 10,006,852; 9,952,076; 9,933,341; 9,726,527; 9,453,789; 9,200,334; 9,097,640; 9,095,494; 9,092,034; 8,975,595; 8,753,573; 8,233,146; 8,140,300; 7,544,326; 7,201,875; 7,129,505; 6,821,740; 6,813,017; 6,809,804; 6,372,506; 5,700,692; 5,643,796; 5,627,040; 5,620,842; 5,602,039; 4,987,086; 4,498,766; the disclosures of which are herein incorporated by reference in their entirety.

In certain instances, flow cytometry systems of the invention are configured for imaging particles in a flow stream by fluorescence imaging using radiofrequency tagged emission (FIRE), such as those described in Diebold, et al. Nature Photonics Vol. 7(10); 806-810 (2013) as well as described in U.S. Pat. Nos. 9,423,353; 9,784,661; 9,983,132; 10,006,852; 10,078,045; 10,036,699; 10,222,316; 10,288,546; 10,324,019; 10,408,758; 10,451,538; 10,620,111; and U.S. Patent Publication Nos. 2017/0133857; 2017/0328826; 2017/0350803; 2018/0275042; 2019/0376895 and 2019/0376894 the disclosures of which are herein incorporated by reference.

Figure 5:
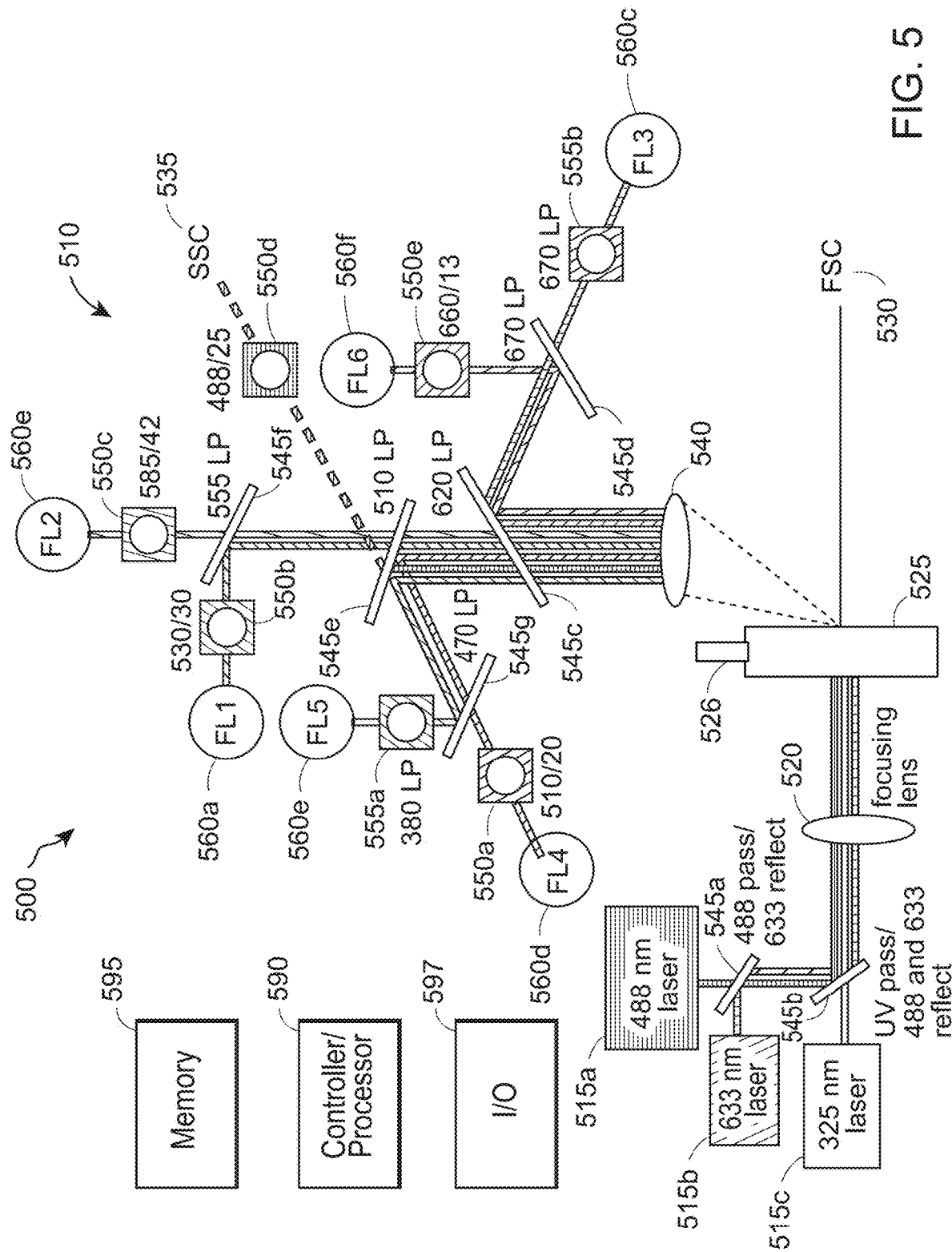
FIG. 5 depicts a functional block diagram of a flow cytometer according to certain embodiments.

FIG. 5 shows a system 500 for flow cytometry in accordance with an illustrative embodiment of the present invention. The system 500 includes a flow cytometer 510, a controller/processor 590 and a memory 595. The flow cytometer 510 includes one or more excitation lasers 515*a*-515*c*, a focusing lens 520, a flow cell 525, a forward-scatter detector 530, a side-scatter detector 535, a fluorescence collection lens 540, one or more beam splitters 545*a*-545*g*, one or more bandpass filters 550*a*-550*e*, one or more long-pass ("LP") filters 555*a*-555*b*, and one or more fluorescent detectors 560*a*-560*f*.

The excitation lasers 515*a*-*c* emit light in the form of a laser beam. The wavelengths of the laser beams emitted from excitation lasers 515*a*-515*c* are 488 nm, 633 nm, and 325 nm, respectively, in the example system of FIG. 5. The laser beams are first directed through one or more of beam splitters 545*a* and 545*b*. Beam splitter 545*a* transmits light at 488 nm and reflects light at 633 nm. Beam splitter 545*b* transmits UV light (light with a wavelength in the range of 10 to 400 nm) and reflects light at 488 nm and 633 nm.

The laser beams are then directed to a focusing lens 520, which focuses the beams onto the portion of a fluid stream where particles of a sample are located, within the flow cell 525. The flow cell is part of a fluidics system which directs particles, typically one at a time, in a stream to the focused laser beam for interrogation. Flow cell 525 includes outlet fitting 526 operably coupled to the distal end (e.g., as discussed above).

The light from the laser beam(s) interacts with the particles in the sample by diffraction, refraction, reflection, scattering, and absorption with re-emission at various different wavelengths depending on the characteristics of the particle such as its size, internal structure, and the presence of one or more fluorescent molecules attached to or naturally present on or in the particle. The fluorescence emissions as well as the diffracted light, refracted light, reflected light, and scattered light may be routed to one or more of the forward-scatter detector 530, the side-scatter detector 535, and the one or more fluorescent detectors 560a-560f through one or more of the beam splitters 545c-545g, the bandpass filters 550a-550e, the longpass filters 555a-555b, and the fluorescence collection lens 540.

The fluorescence collection lens 540 collects light emitted from the particle-laser beam interaction and routes that light towards one or more beam splitters and filters. Bandpass filters, such as bandpass filters 550a-550e, allow a narrow range of wavelengths to pass through the filter. For example, bandpass filter 550a is a 510/20 filter. The first number represents the center of a spectral band. The second number provides a range of the spectral band. Thus, a 510/20 filter extends 10 nm on each side of the center of the spectral band, or from 500 nm to 520 nm. Shortpass filters transmit wavelengths of light equal to or shorter than a specified wavelength. Longpass filters, such as longpass filters 555a-555b, transmit wavelengths of light equal to or longer than a specified wavelength of light. For example, longpass filter 555b, which is a 670 nm longpass filter, transmits light equal to or longer than 670 nm. Filters are often selected to optimize the specificity of a detector for a particular fluorescent dye. The filters can be configured so that the spectral band of light transmitted to the detector is close to the emission peak of a fluorescent dye.

The forward-scatter detector 530 is positioned slightly off axis from the direct beam through the flow cell and is configured to detect diffracted light, the excitation light that travels through or around the particle in mostly a forward direction. The intensity of the light detected by the forward-scatter detector is dependent on the overall size of the particle. The forward-scatter detector can include a photodiode. The side-scatter detector 535 is configured to detect refracted and reflected light from the surfaces and internal structures of the particle that tends to increase with increasing particle complexity of structure. The fluorescence emissions from fluorescent molecules associated with the particle can be detected by the one or more fluorescent detectors 560a-560f. The side-scatter detector 535 and fluorescent detectors can include photomultiplier tubes. The signals detected at the forward-scatter detector 530, the side-scatter detector 535 and the fluorescence detectors can be converted to electronic signals (voltages) by the detectors. This data can provide information about the sample.

One of skill in the art will recognize that a flow cytometer in accordance with an embodiment of the present invention is not limited to the flow cytometer depicted in FIG. 5, but can include any flow cytometer known in the art. For example, a flow cytometer may have any number of lasers, beam splitters, filters, and detectors at various wavelengths and in various different configurations.

In operation, cytometer operation is controlled by a controller/processor 590, and the measurement data from the detectors can be stored in the memory 595 and processed by the controller/processor 590. Although not shown explicitly, the controller/processor 590 is coupled to the detectors to receive the output signals therefrom, and may also be coupled to electrical and electromechanical components of the flow cytometer 510 to control the lasers, fluid flow parameters, and the like. Input/output (I/O) capabilities 597 may be provided also in the system. The memory 595, controller/processor 590, and I/O 597 may be entirely provided as an integral part of the flow cytometer 510. In such an embodiment, a display may also form part of the I/O capabilities 597 for presenting experimental data to users of the cytometer 510. Alternatively, some or all of the memory 595 and controller/processor 590 and I/O capabilities may be part of one or more external devices such as a general purpose computer. In some embodiments, some or all of the memory 595 and controller/processor 590 can be in wireless or wired communication with the cytometer 510. The controller/processor 590 in conjunction with the memory 595 and the I/O 597 can be configured to perform various functions related to the preparation and analysis of a flow cytometer experiment.

The system illustrated in FIG. 5 includes six different detectors that detect fluorescent light in six different wavelength bands (which may be referred to herein as a "filter window" for a given detector) as defined by the configuration of filters and/or splitters in the beam path from the flow cell 525 to each detector. Different fluorescent molecules used for a flow cytometer experiment will emit light in their own characteristic wavelength bands. The particular fluorescent labels used for an experiment and their associated fluorescent emission bands may be selected to generally coincide with the filter windows of the detectors. The I/O 597 can be configured to receive data regarding a flow cytometer experiment having a panel of fluorescent labels and a plurality of cell populations having a plurality of markers, each cell population having a subset of the plurality of markers. The I/O 597 can also be configured to receive biological data assigning one or more markers to one or more cell populations, marker density data, emission spectrum data, data assigning labels to one or more markers, and cytometer configuration data. Flow cytometer experiment data, such as label spectral characteristics and flow cytometer configuration data can also be stored in the memory 595. The controller/processor 590 can be configured to evaluate one or more assignments of labels to markers.

Figure 6:
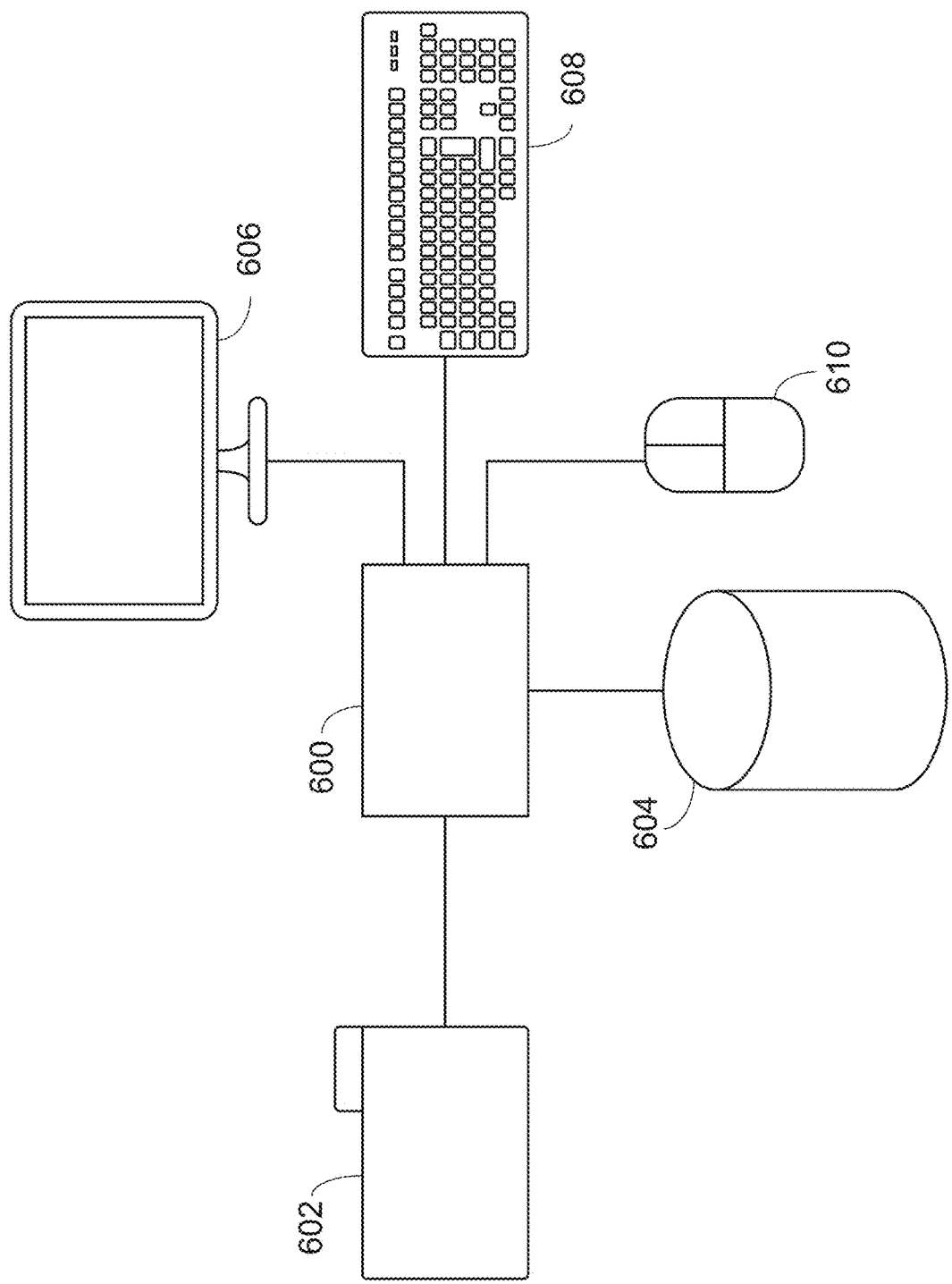
FIG. 6 depicts a flow cytometer control system according to certain embodiments.

FIG. 6 shows a functional block diagram for one example of a control system, such as a processor 600, for analyzing and displaying biological events. A processor 600 can be configured to implement a variety of processes for controlling graphic display of biological events.

A flow cytometer or 602 can be configured to acquire biological event data. For example, a flow cytometer can generate flow cytometric event data (e.g., particle-modulated light data). The flow cytometer 602 can be configured to provide biological event data to the processor 600. A data communication channel can be included between the flow cytometer 602 and the processor 600. The biological event data can be provided to the processor 600 via the data communication channel.

The processor 600 can be configured to receive biological event data from the flow cytometer 602. The biological event data received from the flow cytometer 602 can include flow cytometric event data. The processor 600 can be configured to provide a graphical display including a first plot of biological event data to a display device 606. The processor 600 can be further configured to render a region of interest as a gate around a population of biological event data shown by the display device 606, overlaid upon the first plot, for example. In some embodiments, the gate can be a logical combination of one or more graphical regions of interest drawn upon a single parameter histogram or bivariate plot. In some embodiments, the display can be used to display particle parameters or saturated detector data.

The processor 600 can be further configured to display the biological event data on the display device 606 within the gate differently from other events in the biological event data outside of the gate. For example, the processor 600 can be configured to render the color of biological event data contained within the gate to be distinct from the color of biological event data outside of the gate. The display device 606 can be implemented as a monitor, a tablet computer, a smartphone, or other electronic device configured to present graphical interfaces.

The processor 600 can be configured to receive a gate selection signal identifying the gate from a first input device. For example, the first input device can be implemented as a mouse 610. The mouse 610 can initiate a gate selection signal to the processor 600 identifying the gate to be displayed on or manipulated via the display device 606 (e.g., by clicking on or in the desired gate when the cursor is positioned there). In some implementations, the first device can be implemented as the keyboard 608 or other means for providing an input signal to the processor 600 such as a touchscreen, a stylus, an optical detector, or a voice recognition system. Some input devices can include multiple inputting functions. In such implementations, the inputting functions can each be considered an input device. For example, as shown in FIG. 6, the mouse 610 can include a right mouse button and a left mouse button, each of which can generate a triggering event.

The triggering event can cause the processor 600 to alter the manner in which the data is displayed, which portions of the data is actually displayed on the display device 606, and/or provide input to further processing such as selection of a population of interest for particle sorting.

In some embodiments, the processor 600 can be configured to detect when gate selection is initiated by the mouse 610. The processor 600 can be further configured to automatically modify plot visualization to facilitate the gating process. The modification can be based on the specific distribution of biological event data received by the processor 600. In some embodiments, the processor 600 expands the first gate such that a second gate is generated (e.g., as discussed above).

The processor 600 can be connected to a storage device 604. The storage device 604 can be configured to receive and store biological event data from the processor 600. The storage device 604 can also be configured to receive and store flow cytometric event data from the processor 600. The storage device 604 can be further configured to allow retrieval of biological event data, such as flow cytometric event data, by the processor 600.

The display device 606 can be configured to receive display data from the processor 600. The display data can comprise plots of biological event data and gates outlining sections of the plots. The display device 606 can be further configured to alter the information presented according to input received from the processor 600 in conjunction with input from the flow cytometer 602, the storage device 604, the keyboard 608, and/or the mouse 610.

Methods of Analyzing a Sample

Aspects of the invention further include methods of analyzing a sample. Methods of interest include introducing a sample into a flow cytometer comprising a flow channel for transporting particles in a flow stream therethrough from an inlet at a proximal end to an outlet at a distal end, a light source for irradiating the flow stream at an interrogation point, a detector for receiving particle-modulated light from the flow stream, and an outlet fitting. As discussed above, outlet fittings of interest include an elongate structure and an opening at a proximal end for receiving the flow stream from the distal end of the flow cell. In addition, outlet fittings described herein configured to reduce the formation of bubbles at the interface between the outlet fitting and the flow cell, and operably couple to a waste line at a distal end. Methods of the present disclosure subsequently involve flow cytometrically analyzing the sample.

In some instances, the sample analyzed in the instant methods is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class Mammalia, including the orders carnivore (e.g., dogs and cats), Rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

Cells of interest may be targeted for characterized according to a variety of parameters, such as a phenotypic characteristic identified via the attachment of a particular fluorescent label to cells of interest. In some embodiments, the system is configured to deflect analyzed droplets that are determined to include a target cell. A variety of cells may be characterized using the subject methods. Target cells of interest include, but are not limited to, stem cells, T cells, dendritic cells, B Cells, granulocytes, leukemia cells, lymphoma cells, virus cells (e.g., HIV cells), NK cells, macrophages, monocytes, fibroblasts, epithelial cells, endothelial cells, and erythroid cells. Target cells of interest include cells that have a convenient cell surface marker or antigen that may be captured or labelled by a convenient affinity agent or conjugate thereof. For example, the target cell may include a cell surface antigen such as CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71. In some embodiments, the target cell is selected from HIV containing cell, a Treg cell, an antigen-specific T-cell populations, tumor cells or hematopoietic progenitor cells (CD34+) from whole blood, bone marrow or cord blood.

In practicing the subject methods, a sample (e.g., in a flow stream of a flow cytometer) is irradiated with light from a light source. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Where methods include irradiating with a broadband light source, broadband light source protocols of interest may include, but are not limited to, a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, methods includes irradiating with a narrow band light source emitting a particular wavelength or a narrow range of wavelengths, such as for example with a light source which emits light in a narrow range of wavelengths like a range of 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Where methods include irradiating with a narrow band light source, narrow band light source protocols of interest may include, but are not limited to, a narrow wavelength LED, laser diode or a broadband light source coupled to one or more optical bandpass filters, diffraction gratings, monochromators or any combination thereof.

In certain embodiments, methods include irradiating the sample with one or more lasers. As discussed above, the type and number of lasers will vary depending on the sample as well as desired light collected and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In other instances, the methods include irradiating the flow stream with a dye laser, such as a stilbene, coumarin or rhodamine laser. In yet other instances, methods include irradiating the flow stream with a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, methods include irradiating the flow stream with a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof.

The sample may be irradiated with one or more of the above mentioned light sources, such as 2 or more light sources, such as 3 or more light sources, such as 4 or more light sources, such as 5 or more light sources and including 10 or more light sources. The light source may include any combination of types of light sources. For example, in some embodiments, the methods include irradiating the sample in the flow stream with an array of lasers, such as an array having one or more gas lasers, one or more dye lasers and one or more solid-state lasers.

The sample may be irradiated with wavelengths ranging from 200 nm to 1500 nm, such as from 250 nm to 1250 nm, such as from 300 nm to 1000 nm, such as from 350 nm to 900 nm and including from 400 nm to 800 nm. For example, where the light source is a broadband light source, the sample may be irradiated with wavelengths from 200 nm to 900 nm. In other instances, where the light source includes a plurality of narrow band light sources, the sample may be irradiated with specific wavelengths in the range from 200 nm to 900 nm. For example, the light source may be plurality of narrow band LEDs (1 nm-25 nm) each independently emitting light having a range of wavelengths between 200 nm to 900 nm. In other embodiments, the narrow band light source includes one or more lasers (such as a laser array) and the sample is irradiated with specific wavelengths ranging from 200 nm to 700 nm, such as with a laser array having gas lasers, excimer lasers, dye lasers, metal vapor lasers and solid-state laser as described above.

Where more than one light source is employed, the sample may be irradiated with the light sources simultaneously or sequentially, or a combination thereof. For example, the sample may be simultaneously irradiated with each of the light sources. In other embodiments, the flow stream is sequentially irradiated with each of the light sources. Where more than one light source is employed to irradiate the sample sequentially, the time each light source irradiates the sample may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. For example, methods may include irradiating the sample with the light source (e.g. laser) for a duration which ranges from 0.001 microseconds to 100 microseconds, such as from 0.01 microseconds to 75 microseconds, such as from 0.1 microseconds to 50 microseconds, such as from 1 microsecond to 25 microseconds and including from 5 microseconds to 10 microseconds. In embodiments where sample is sequentially irradiated with two or more light sources, the duration sample is irradiated by each light source may be the same or different.

The time period between irradiation by each light source may also vary, as desired, being separated independently by a delay of 0.001 microseconds or more, such as 0.01 microseconds or more, such as 0.1 microseconds or more, such as 1 microsecond or more, such as 5 microseconds or more, such as by 10 microseconds or more, such as by 15 microseconds or more, such as by 30 microseconds or more and including by 60 microseconds or more. For example, the time period between irradiation by each light source may range from 0.001 microseconds to 60 microseconds, such as from 0.01 microseconds to 50 microseconds, such as from 0.1 microseconds to 35 microseconds, such as from 1 microsecond to 25 microseconds and including from 5 microseconds to 10 microseconds. In certain embodiments, the time period between irradiation by each light source is 10 microseconds. In embodiments where sample is sequentially irradiated by more than two (i.e., 3 or more) light sources, the delay between irradiation by each light source may be the same or different.

The sample may be irradiated continuously or in discrete intervals. In some instances, methods include irradiating the sample in the sample with the light source continuously. In other instances, the sample in is irradiated with the light source in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

Depending on the light source, the sample may be irradiated from a distance which varies such as 0.01 mm or more, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more. Also, the angle or irradiation may also vary, ranging from 10° to 90°, such as from 15° to 85°, such as from 20° to 80°, such as from 25° to 75° and including from 30° to 60°, for example at a 90° angle.

As discussed above, in embodiments light from the irradiated sample is conveyed to a light detection system as described herein and measured by one or more photodetectors. In practicing the subject methods, light from the sample is conveyed to three or more wavelength separators that are each configured to pass light having a predetermined spectral range. The spectral ranges of light from each of the wavelength separators are conveyed to one or more light detection modules having optical components that are configured to convey light having a predetermined sub-spectral range to the photodetectors.

Light may be measured with the light detection systems continuously or in discrete intervals. In some instances, methods include taking measurements of the light continuously. In other instances, the light is measured in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Measurements of the collected light may be taken one or more times during the subject methods, such as 2 or more times, such as 3 or more times, such as 5 or more times and including 10 or more times. In certain embodiments, the light propagation is measured 2 or more times, with the data in certain instances being averaged.

In some embodiments, methods include adjusting the light before detecting the light with the subject light detection systems. For example, the light from the sample source may be passed through one or more lenses, mirrors, pinholes, slits, gratings, light refractors, and any combination thereof. In some instances, the collected light is passed through one or more focusing lenses, such as to reduce the profile of the light directed to the light detection system or optical collection system as described above. In other instances, the emitted light from the sample is passed through one or more collimators to reduce light beam divergence conveyed to the light detection system.

Methods of Assembling a Flow Cytometer

Aspects of the disclosure further include methods of assembling a flow cytometer. Methods of interest include operably attaching an outlet fitting to a flow cell of the flow cytometer. As discussed above, flow cells of interest include a flow channel for transporting particles in a flow stream therethrough from an inlet at a proximal end to an outlet at a distal end. In addition, outlet fittings of interest have an elongate structure and an opening at a proximal end for receiving the flow stream from the distal end of the flow cell, and are configured to reduce the formation of bubbles at the interface between the outlet fitting and the flow cell. In certain cases, the disclosed outlet fittings do not include a planar surface in contact with the received flow stream. For example, in some instances, the outlet fitting includes an annular lip surrounding the opening for establishing a gapless interface between the outlet fitting and the distal end of the flow cell. In additional cases, the opening is tapered.

In some embodiments where the subject outlet fittings include an annular lip, methods include engaging the annular lip in a face seal with the flow cell. In certain cases, methods involve engaging the annular lip in a face seal with the cuvette of the flow cell. In some instances, fluidically sealing the flow cell and the outlet fitting additionally includes inserting an O-ring into the O-ring groove of the outlet fitting (e.g., such that fluid does not escape the through the interface in a radial direction).

Where desired, methods further include operably coupling a waste line to the outlet fitting. As discussed above, embodiments of the outlet fitting include a connector at the distal end for providing a connection with the waste line. As such, in certain cases, methods include operably coupling the waste line to the outlet fitting via the connector. In additional embodiments, methods include operably attaching a vacuum source to the waste line, i.e., such that fluid in the flow stream may be drawn through the outlet fitting and into the waste line. Methods of interest may additionally include operably attaching a waste container to the waste line, i.e., for the storage and/or disposal of the waste fluid.

Computer Controlled Systems

Aspects of the present disclosure further include computer-controlled systems, where the systems include one or more computers for complete automation or partial automation. In some embodiments, systems include a computer having a non-transitory computer readable storage medium with a computer program stored thereon, where the computer program when loaded on the computer includes instructions for analyzing data produced by a flow cytometer having the subject outlet flitting.

In embodiments, the system includes an input module, a processing module, and an output module. The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor, or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, Python, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques. In some embodiments, the processor includes analog electronics which provide feedback control, such as for example negative feedback control.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, or a diskette drive. Such types of memory storage devices typically read from, and/or write to, a program storage medium (not shown) such as a compact disk. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid-state storage devices (including magnetic or optical disks or tape or RAM, or any other suitable device, either fixed or portable). The processor may include a general-purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, Wi-Fi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, a USB-C port, an RS-232 port, or any other suitable electrical connection port to allow data communication between the subject systems and other external devices such as a computer terminal (for example, at a physician's office or in hospital environment) that is configured for similar complementary data communication.

In one embodiment, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or Wi-Fi connection to the internet at a Wi-Fi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a workstation, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows® NT®, Windows® XP, Windows® 7, Windows® 8, Windows® 10, iOS®, macOS®, Linux®, Ubuntu®, Fedora®, OS/400®, i5/OS®, IBM i®, Android™, SGI IRIX®, Oracle Solaris® and others.

Figure 7:
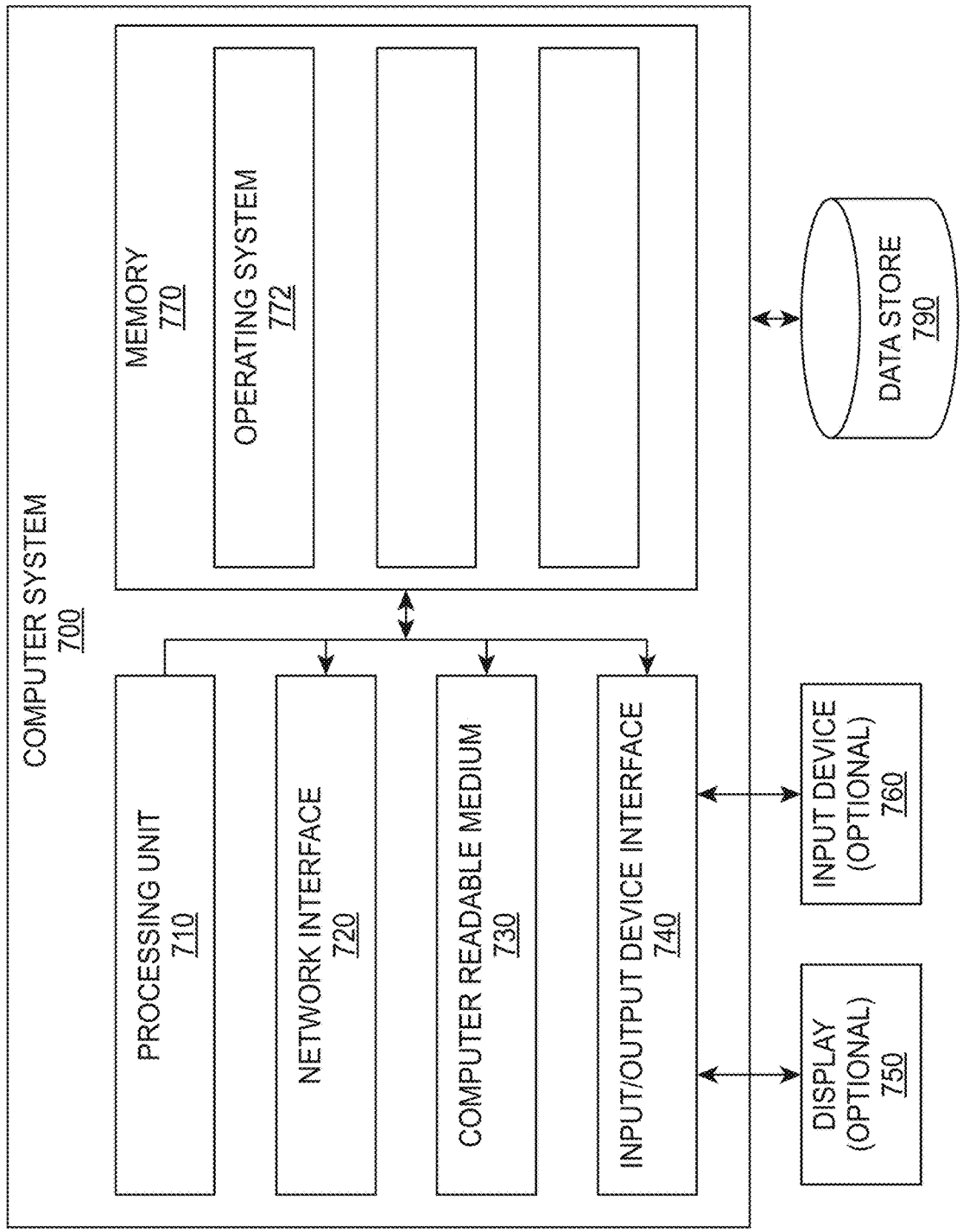
FIG. 7 depicts a block diagram of a computing system according to certain embodiments.

FIG. 7 depicts a general architecture of an example computing device 700 according to certain embodiments. The general architecture of the computing device 700 depicted in FIG. 7 includes an arrangement of computer hardware and software components. It is not necessary, however, that all of these generally conventional elements be shown in order to provide an enabling disclosure. As illustrated, the computing device 700 includes a processing unit 710, a network interface 720, a computer readable medium drive 730, an input/output device interface 740, a display 750, and an input device 760, all of which may communicate with one another by way of a communication bus. The network interface 720 may provide connectivity to one or more networks or computing systems. The processing unit 710 may thus receive information and instructions from other computing systems or services via a network. The processing unit 710 may also communicate to and from memory 770 and further provide output information for an optional display 750 via the input/output device interface 740. For example, an analysis software (e.g., data analysis software or program such as FlowJo®) stored as executable instructions in the non-transitory memory of the analysis system can display the flow cytometry event data to a user. The input/output device interface 740 may also accept input from the optional input device 760, such as a keyboard, mouse, digital pen, microphone, touch screen, gesture recognition system, voice recognition system, gamepad, accelerometer, gyroscope, or other input device.

The memory 770 may contain computer program instructions (grouped as modules or components in some embodiments) that the processing unit 710 executes in order to implement one or more embodiments. The memory 770 generally includes RAM, ROM and/or other persistent, auxiliary or non-transitory computer-readable media. The memory 770 may store an operating system 772 that provides computer program instructions for use by the processing unit 710 in the general administration and operation of the computing device 700. Data may be stored in data storage device 790. The memory 770 may further include computer program instructions and other information for implementing aspects of the present disclosure.

Utility

The subject light detection systems find use where the characterization of a sample by optical properties is desired. In particular, the present invention may be employed where it is desirable to reduce the formation of bubbles at the interface between an outlet fitting and flow cell, and thereby reduce laser delay. In some embodiments, the systems and methods described herein find use in flow cytometry characterization of biological samples labelled with fluorescent tags. In other embodiments, the systems and methods find use in spectroscopy of transmitted or scattered light. In addition, the subject systems and methods find use in increasing the obtainable signal from light collected from a sample (e.g., in a flow stream). In certain instances, the present disclosure finds use in enhancing measurement of light collected from a sample that is irradiated in a flow stream in a flow cytometer. Embodiments of the present disclosure find use where enhancing the effectiveness of emission measurements in flow cytometry are desired, such as in research and high throughput laboratory testing.

Kits

Aspects of the invention further include kits, where kits include one or more outlet fittings. As discussed above, outlet fittings of interest include an elongate structure and an opening at a proximal end for receiving a flow stream from the distal end of a flow cell. In addition, an outlet fitting for use in the subject kits is configured to reduce the formation of bubbles at the interface between the outlet fitting and the flow cell, and operably couple to a waste line at a distal end. In some cases, the disclosed outlet fitting does not include a planar surface that is orthogonal to the direction of fluid flow of the received flow stream (e.g., the outlet fitting includes an annular lip and/or tapered opening). Kits may include any suitable number of outlet fittings. For example, in some instances, kits include a single outlet fitting. In other instances, kits include a plurality of outlet fittings, such as where the number of outlet fittings ranges from 2 to 10.

Embodiments of the subject kits additionally include one or more waste lines for operably coupling to the distal end of an outlet fitting. Kits may include any suitable number of waste lines. For example, in some instances, kits include a single waste line. In other instances, kits include a plurality of waste lines, such as where the number of waste lines ranges from 2 to 10. In some instances, kits additionally include a flow cell. In such instances, kits may include one or more cuvettes for use in the flow cell. Kits may include any suitable number of cuvettes. In some cases, kits include a single cuvette. In other cases, kits include a plurality of cuvettes, such as where the number of cuvettes ranges from 2 to 10.

In addition to the above components, the subject kits may further include (in some embodiments) instructions, e.g., for assembly of a flow cytometer having the described outlet fitting and/or instructions for the use of such a flow cytometer. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

The following example is offered by way of illustration and not by way of limitation.

EXPERIMENTAL

A FACSLyric™ particle analyzer (BD Biosciences) was modified to include a camera for monitoring the interface between the cuvette and the outlet fitting. Once a sample containing beads was running in the cell analyzer, air was introduced into the system via the sample line. Bubbles trapped at the interface between the cuvette and outlet fitting were subsequently observed via the camera.

A new outlet fitting having a reduced gap was manufactured and installed on the same FACSLyric™ particle analyzer. Once sample was running, air was introduced to the system via the sample line. The resulting bubbles passed through the system and were not trapped at the interface.

Although the foregoing invention has been described in some detail by way of illustration and example for purposes of clarity of understanding, it is readily apparent to those of ordinary skill in the art in light of the teachings of this invention that some changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112(f) or 35 U.S.C. § 112(6) is not invoked.

What is claimed is:

1. A flow cytometer comprising:
    a flow cell comprising a flow channel for transporting particles in a flow stream therethrough from an inlet at a proximal end to an outlet at a distal end;
    a light source for irradiating the flow stream at an interrogation point;
    a detector configured to receive particle-modulated light from the flow stream; and
    an outlet fitting comprised of an elongate structure and an opening at a proximal end of the elongate structure for receiving the flow stream from the distal end of the flow cell, wherein the outlet fitting is configured to reduce the formation of bubbles at the interface between the outlet fitting and the flow cell, and operably couple to a waste line at a distal end of the elongate structure.

2. The flow cytometer according to claim 1, wherein the outlet fitting does not include a planar surface that is orthogonal to the direction of fluid flow of the received flow stream and is configured to contact the flow stream.

3. The flow cytometer according to claim 1, wherein the outlet fitting comprises an annular lip surrounding the opening for establishing a gapless interface between the outlet fitting and the distal end of the flow cell.

4. The flow cytometer according to claim 3, wherein the annular lip is engaged in a face seal with the flow cell.

5. The flow cytometer according to claim 3, wherein the annular lip has a diameter ranging from 1.5 mm to 2.5 mm.

6. The flow cytometer according to claim 5, wherein the annular lip has a diameter ranging from 1.6 mm to 2 mm.

7. The flow cytometer according to claim 1, wherein the opening is tapered.

8. The flow cytometer according to claim 7, wherein the opening has a taper angle ranging from 1° to 60°.

9. The flow cytometer according to claim 8, wherein the opening has a taper angle ranging from 1° to 20°.

10. The flow cytometer according to claim 1, wherein the opening has a diameter ranging from 0.5 mm to 2.5 mm.

11. The flow cytometer according to claim 10, wherein the opening has a diameter ranging from 0.5 mm to 0.7 mm.

12. The flow cytometer according to claim 1, wherein the outlet fitting comprises an O-ring groove.

13. The flow cytometer according to claim 12, further comprising an O-ring matched to the size of the O-ring groove.

14. The flow cytometer according to claim 1, wherein the flow cell comprises a cuvette.

15. The flow cytometer according to claim 1, further comprising a waste line operably coupled to the outlet fitting.

16. The flow cytometer according to claim 15, further comprising a vacuum source operably coupled to the waste line.

17. The flow cytometer according to claim 1, wherein the outlet fitting is comprised of a polymeric material.

18. The flow cytometer according to claim 17, wherein the outlet fitting is comprised of polyether ether ketone (PEEK).

19. The flow cytometer according to claim 1, wherein the flow cytometer comprises a plurality of detectors.

20. The flow cytometer according to claim 1, wherein:
    the outlet fitting comprises a channel running therethrough from a proximal end to a distal end, and;
    the opening and the channel have the same diameter.

* * * * *